(12) United States Patent
Nojima et al.

(10) Patent No.: US 8,206,924 B2
(45) Date of Patent: Jun. 26, 2012

(54) TRACE MRNA AMPLIFICATION METHOD AND USE THEREOF

(75) Inventors: Hiroshi Nojima, Suita (JP); Takahiro Tougan, Suita (JP); Daisuke Okuzaki, Suita (JP)

(73) Assignee: Osaka University, Osaka (JP)

( * ) Notice: Subject to any disclaimer, the term of this patent is extended or adjusted under 35 U.S.C. 154(b) by 362 days.

(21) Appl. No.: 12/310,846

(22) PCT Filed: Aug. 29, 2007

(86) PCT No.: PCT/JP2007/066808
§ 371 (c)(1),
(2), (4) Date: Mar. 10, 2009

(87) PCT Pub. No.: WO2008/032574
PCT Pub. Date: Mar. 20, 2008

(65) Prior Publication Data
US 2009/0312199 A1    Dec. 17, 2009

(30) Foreign Application Priority Data
Sep. 11, 2006    (JP) .................................. 2006-246053

(51) Int. Cl.
C12Q 1/68    (2006.01)
C12P 19/34    (2006.01)
C07H 21/02    (2006.01)

(52) U.S. Cl. ....................... 435/6.12; 435/91.2; 536/23.1

(58) Field of Classification Search ........................ None
See application file for complete search history.

(56) References Cited

U.S. PATENT DOCUMENTS

| 6,022,715 | A | * | 2/2000 | Merenkova et al. ............... 435/6 |
| 6,300,075 | B1 | | 10/2001 | Preston et al. |
| 2004/0086906 | A1 | | 5/2004 | Takiguchi |
| 2005/0003392 | A1 | * | 1/2005 | Salceda et al. ..................... 435/6 |
| 2005/0064472 | A1 | | 3/2005 | Shekar et al. |

FOREIGN PATENT DOCUMENTS

| EP | 1 362 912 | 11/2003 |
| EP | 1 767 620 | 3/2007 |
| JP | 2002-238575 | 8/2002 |

OTHER PUBLICATIONS

Fujii, T. et al, Use of stepwise substraction to comprehensively isolate mouse genes whose transcription is up-regulated during spermiogenesis, EMBO Reports, 2002, vol. 3, No. 4, pp. 367-372.
Nierman, W.C. and Chamberlin, M. J., The effect of low substrate concentrations on the extent of productiveRNA chain initiation from T7 promoters A1 and A2 by *Escherichia coli* RNApolymerase, Journal of Biological Chemistry, 1980, vol. 255, No. 10, pp. 4495-4500.
European Search Report dated May 11, 2010 issued in corresponding European application No. 07806285.8-1222.
T. Kievits, et al., "*NABA™ isothermal enzymatic in vitro nucleic acid amplification optimized for the diagnosis of HIV-1 infection*", Journal of Virological Methods, vol. 35, pp. 273-286 (1991).
A. Ylikoski, et al., "*Quantitative Reverse Transcription-PCR Assay with an Internal Standard for the Detection of Prostate-specific Antigen mRNA*," Clinical Chemistry, vol. 45:9, pp. 1397-1407 (1999).
K. Aoyagi, et al., "*A faithful method for PCR-mediated global mRNA amplification and its integration into microarray analysis on laer-captured cells*," Biochemical and Biophysical Research Communications, vol. 300, pp. 915-920 (2003).
J. Eberwine, et al.,"*Analysis of gene expression in single live neurons*," Proc. Natl. Acad. Sci. USA, vol. 89, pp. 3010-3014 (1992).
Office Action dated Feb. 21, 2011 for corresponding Canadian Patent Application No. 2,662,931.
Wang, E., et al. (2000) "High-fidelity mRNA amplification for gene profiling" Nature Biotechnology, 18:457-459.
EP Examination Report for Application No. 07 806 285.8 dated Jan. 13, 2012.
Stahlberg, et al. (2004) "Properties of the reverse Transcription Reaction in mRNA Quantification" Clinical Chemistry, 50: 3, pp. 509-515.
Canadian Office Action for Canadian Application No. 2,662,931 Dated Jan. 11, 2012.

* cited by examiner

*Primary Examiner* — Angela M Bertagna
(74) *Attorney, Agent, or Firm* — Harness, Dickey & Pierce, P.L.C.

(57) ABSTRACT

A method for amplifying a trace amount of mRNA includes adding a dummy RNA to a solution containing the trace amount of mRNA, so as to prepare a mixed solution; synthesizing an anti-sense DNA by reverse transcription, which uses the mixed solution as a template; synthesizing a sense DNA which is complementary to the anti-sense DNA thus synthesized, so as to generate a double-strand DNA made of the sense DNA and the anti-sense DNA; ligating an RNA polymerase promoter sequence to the double-strand DNA thus generated, on a sense DNA 5' end side of the double-strand DNA, so as to prepare a double-strand DNA for amplification; and amplifying, by using RNA polymerase, an RNA from the double-strand DNA for amplification.

8 Claims, 13 Drawing Sheets

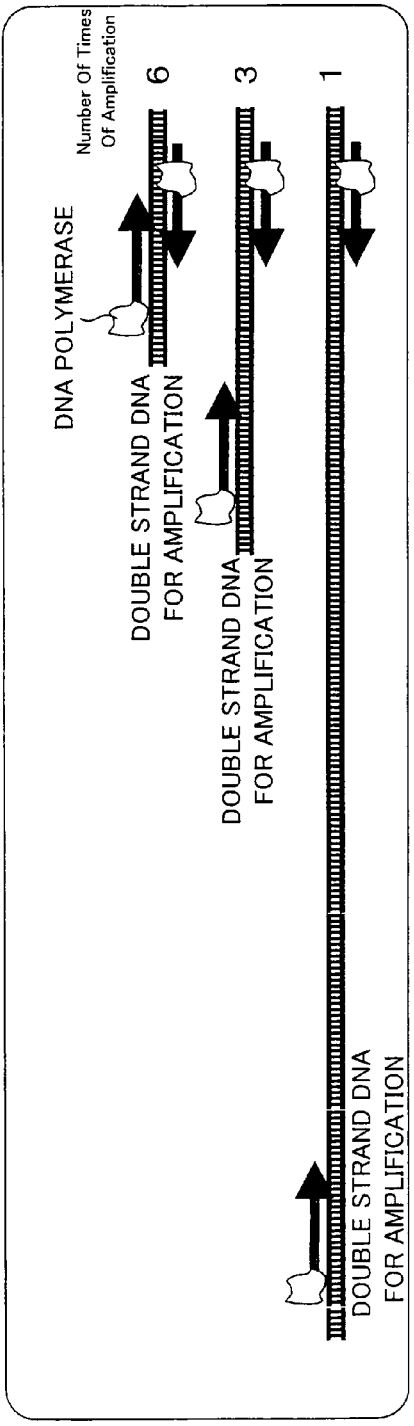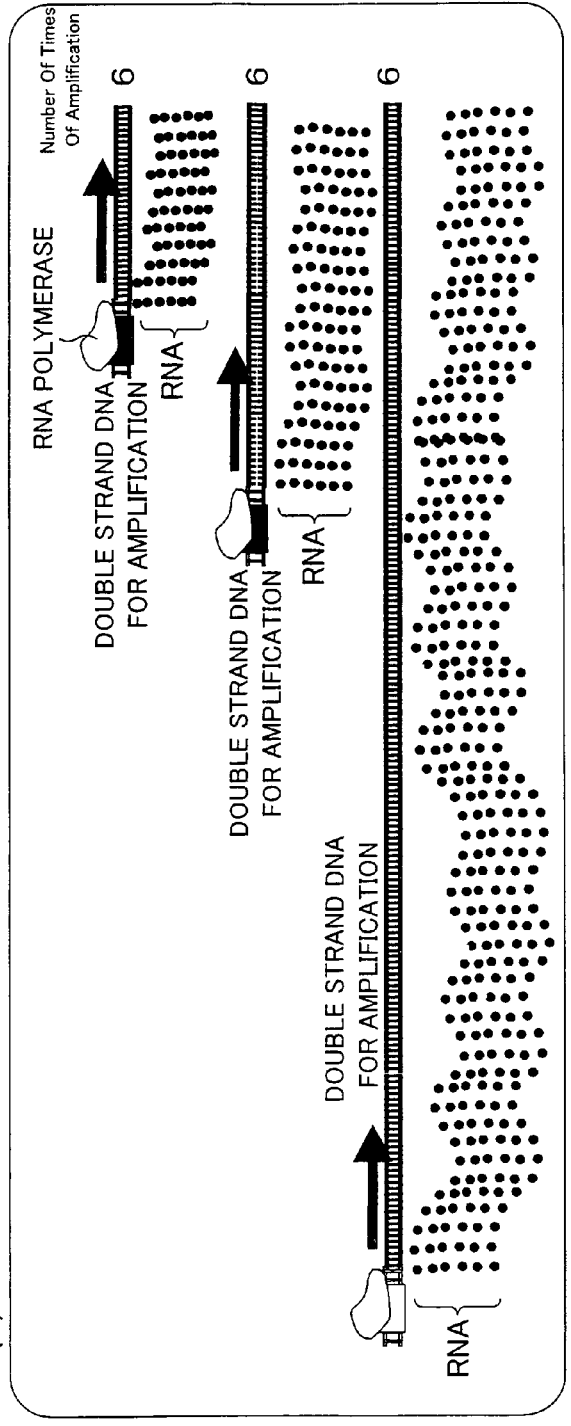
FIG. 1(a)
FIG. 1(b)

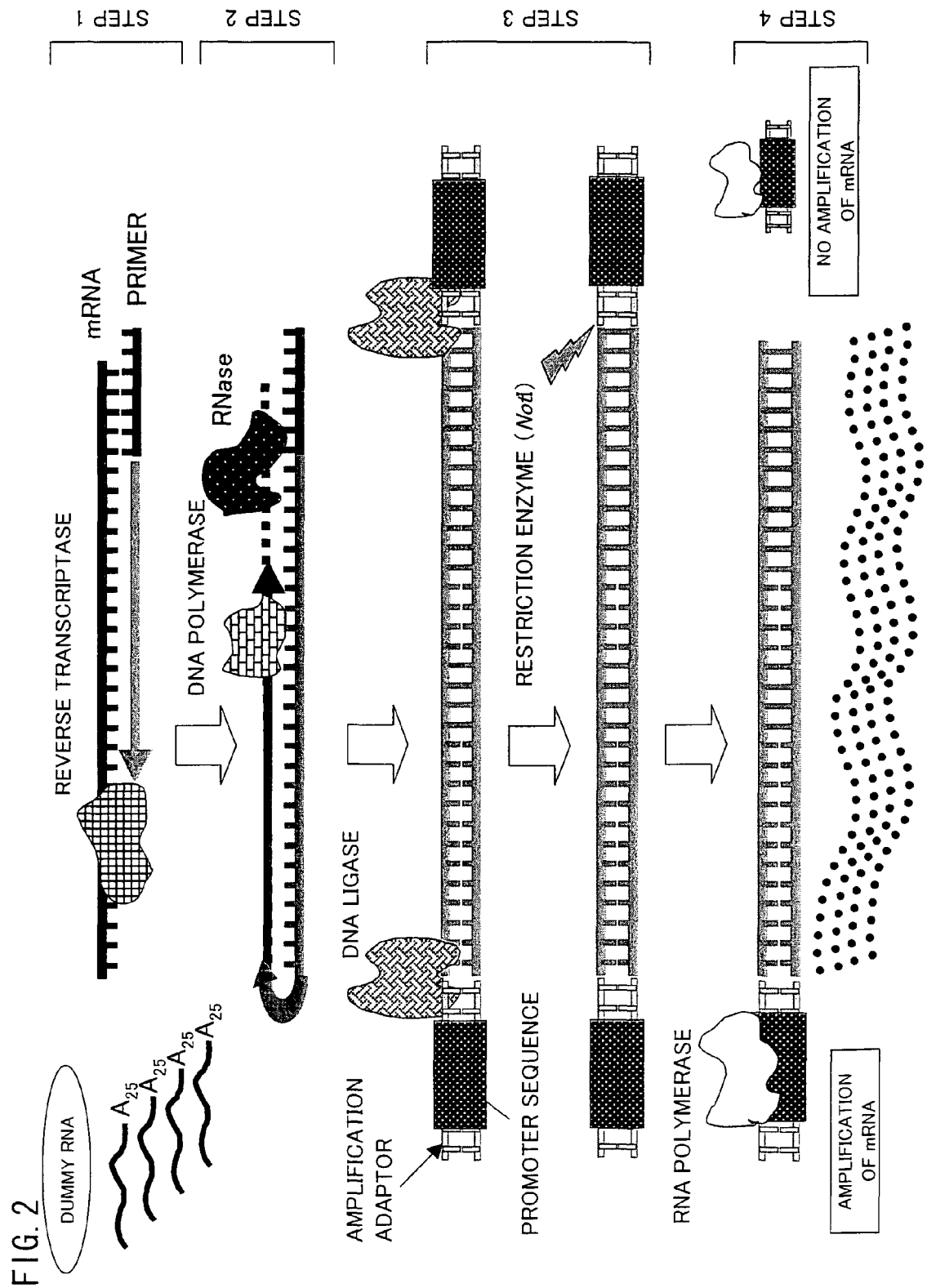

TRACE MRNA AMPLIFICATION METHOD AND USE THEREOF

TECHNICAL FIELD

The present invention relates to a method for amplifying a trace amount of mRNA and use thereof. More specifically, the present invention relates to a method for amplifying a trace amount of mRNA and use thereof, each of which is suitably applicable to preparation of a cDNA library, amplification of a sense strand of an mRNA, preparation of a labeled probe in which the sense strand of the mRNA is encoded, stepwise subtraction, and the like.

BACKGROUND ART

Conventionally, a method in which a cDNA library or the like is analyzed has been known as one of analysis methods of genes. The cDNA library is prepared by purifying an mRNA from a cell, and synthesizing a cDNA from this mRNA. In this case, a very small amount of the mRNA can usually be purified from the cell. In a case where the mRNA is purified from cells that exists in mass amount in a living body, it is possible to obtain a sufficient amount of the mRNA for synthesizing a cDNA library by using a large amount of cells for the purification of the mRNA. However, if the mRNA is to be purified from a cell that is in a very small number in the living body (for example, a stem cell, germ cell or the like), there is a great limit in the amount of the mRNA that can be used for synthesizing the cDNA library. In this case, there is a need to amplify the purified mRNA. Accordingly, methods for amplifying a trace amount of mRNA have been conventionally developed.

As the mRNA amplification method as above, a method which amplifies the mRNA by PCR is generally adopted. The following describes more details of the mRNA amplification method. First, mRNA is purified from a cell. Next, cDNA is prepared by reverse-transcription. Subsequently, a double strand DNA is prepared by using a DNA polymerase and the cDNA as a template. This double strand DNA is then amplified by PCR. Finally, the amplified double strand. DNA is treated with an RNA polymerase so as to prepare the mRNA. In this way, an amplified mRNA is obtained (for example, see Patent Document 1).

PATENT CITATION

Patent Literature 1

Japanese Unexamined Patent Publication No. 238575/2002 (Tokukai 2002-238575; published on Aug. 27, 2002)

However, the method which amplifies the mRNA by use of PCR as described in Patent Literature 1 has a problem in that a short mRNA and a long mRNA are amplified with different efficiency levels.

More specifically, PCR is capable of efficiently amplifying a short base sequence, however is difficult to efficiently amplify a long base sequence. Therefore, a method in which a double strand DNA for amplification that serves as a template of an mRNA is amplified by use of PCR, as in the method in Patent Literature 1, is capable of efficiently amplifying the double strand DNA for amplification if the double strand DNA has a short base sequence, however is not capable of efficiently amplifying the double strand DNA for amplification if the double strand DNA has a long base sequence. That is to say, the double strand DNA that will serve as a template in the mRNA synthesis is amplified in different amounts depending on how long the base sequence of the double strand DNA is. Hence, the mRNA amplification by use of the double strand DNA amplified by the PCR faces such a problem that the short mRNA can be efficiently amplified, but the long mRNA cannot be amplified in a same efficiency level as the short mRNA. This disadvantage becomes a large issue in a case where a highly-diversified cDNA library is to be prepared. In other words, the conventional method has a problem in that quantitative distribution of mRNA (cDNA) becomes significantly different before and after the amplification, even though it is most important in the cDNA library that the mRNA is amplified identically in quantitative distribution.

Hence, there has been a strong demand for development of a method for amplifying a trace amount of mRNA that is capable of amplifying the short mRNA and the long mRNA in a same degree of efficiency level, regardless of the length of the base sequence.

DISCLOSURE OF INVENTION

The present invention is accomplished in view of the conventional problem, and an object of the present invention is to provide a method for amplifying a trace amount of mRNA which can efficiently amplify a long mRNA as well as a short mRNA, regardless of a length of a base sequence.

As a result of diligent study in order to solve the problem, the inventors of the present invention found that, in order to deal with a case where merely a trace amount of the mRNA to be amplified is included in the reacting solution, an amount of a double strand DNA for amplification can be increased up to an optimum substrate concentration (in the order of millimole (mM)) of the RNA polymerase, by adding a dummy RNA to a reacting solution in synthesis of the double strand DNA for amplification. This remarkably improved RNA synthesis reaction rate that had been extremely slow due to a low substrate concentration. This allowed an efficient mRNA amplification. According to this technique, there is no need to carry out a step of amplifying the double strand DNA by PCR. Therefore, the inventors demonstrated that it is possible to amplify mRNA efficiently regardless of the length of its base sequence, thereby accomplishing the present invention. The present invention is accomplished on a basis of this new finding, and includes the following inventions.

That is to say, in order to attain the object, a method of the present invention for amplifying a trace amount of mRNA includes the steps of: (i) adding a dummy RNA to a solution containing the trace amount of mRNA, so as to prepare a mixed solution; (ii) synthesizing an anti-sense DNA by reverse transcription that uses the mixed solution as a template; (iii) synthesizing a sense DNA which is complementary to the anti-sense DNA thus synthesized, so as to generate a double strand DNA made of the sense DNA and the anti-sense DNA; (iv) ligating an RNA polymerase promoter sequence to the double strand DNA thus generated, on a sense DNA 5' end side of the double strand DNA, so as to prepare a double strand DNA for amplification; and (v) amplifying, by using RNA polymerase, an RNA from the double strand DNA for amplification.

According to the arrangement, an amount of RNA contained in a mixed solution is increased by addition of a dummy RNA to a trace amount of mRNA. As a result, an amount of a double strand DNA for amplification that is prepared increases as compared to a case where the RNA contained in the mixed solution is only the trace amount of mRNA. In this case, the amount of the double strand DNA for amplification is adjusted to optimum concentration of RNA polymerase. This thus allows progression of transcription by the RNA polymerase. Hence, it is possible to amplify short mRNA and long mRNA in a same efficiency level, regardless of a length of a base sequence.

Namely, the method of the present invention for amplifying the trace amount of mRNA is characterized in a point that an initial RNA concentration is increased by use of the dummy RNA so as to solve a problem of difficulty in progression of transcription, which problem is caused by initially having only a small amount of RNA, thereby causing the amount of the double strand DNA to be small in amount.

Moreover, in the method of the invention for amplifying the trace amount of mRNA, it is preferable for the step (iv) to include a step (vi) of ligating the promoter sequence to both ends of the double strand DNA thus generated in the step (iii), and cleaving the promoter sequence off from the double strand DNA only on the sense DNA 3' end side.

According to the arrangement, it is possible to selectively transcribe just the sense strand of the trace amount of mRNA and the dummy RNA, and as a result amplify just the sense strand.

Moreover, in the method of the present invention for amplifying the trace amount of mRNA, it is preferable for the step (iv) to generate a restriction enzyme site on the double strand DNA, on the sense DNA 3' end side of the double strand DNA, so as to cleave the promoter sequence off from the double strand DNA only on the sense DNA 3' end side.

Moreover, in the method of the present invention for amplifying the trace amount of mRNA, it is preferable for the step (iv) to include a step (vii) of removing the promoter sequence thus cleaved off and the dummy RNA.

According to the arrangement, when the RNA is amplified by the RNA polymerase, it is possible to transcribe the RNA by just the promoter sequence ligated to the double strand DNA on the sense DNA 5' end side of the double strand DNA while avoiding the RNA polymerase to not bind to the promoter sequence that is cleaved off.

In the method of the present invention for amplifying the trace amount of mRNA, it is preferable for a sequence of the dummy RNA to include a poly(A) sequence.

Moreover, in the method of the present invention for amplifying the trace amount of mRNA, it is preferable for the sequence of the dummy RNA to be a base sequence indicated by sequence number 4, 6, or 16.

According to the arrangement, the trace amount of mRNA and the dummy RNA both have a poly(A) sequence. Therefore, the trace amount of mRNA and the dummy RNA can be simultaneously reverse-transcribed by use of an identical primer that contains an oligo-dT sequence.

In the method of the present invention for amplifying the trace amount of mRNA, it is preferable for the dummy RNA to be biotinylated.

According to the present arrangement, a biotinylated dummy RNA can be specifically bind to streptavidin. Therefore, it is possible to specifically remove just the dummy RNA from the reaction solution by use of a streptavidin column or the like.

Moreover, in the method of the present invention for amplifying the trace amount of mRNA, it is preferable for the RNA polymerase to be T7 polymerase, T3 polymerase, or SP6 polymerase.

With the arrangement, it is possible to efficiently transcribe the trace amount of the mRNA and the dummy RNA.

Moreover, in the method of the present invention for amplifying the trace amount of mRNA, it is preferable for a dummy RNA concentration in the mixed solution to be in a range of 0.5 to 10 µg/µL.

With the arrangement, it is possible to prepare a double strand DNA for amplification which has a concentration that is suitable for reaction of the RNA polymerase. As a result, amplification of the trace amount of mRNA that could not be amplified due to its slow transcription speed is possible.

In order to attain the object, a method of the present invention for preparing a cDNA library preferably includes the method for amplifying the trace amount of mRNA.

According to the arrangement, even if the initial amount of the mRNA is trace, the mRNA can be efficiently amplified. Thus, it is possible to prepare a cDNA library from the trace amount of the mRNA.

In order to attain the object, a method of the present invention for preparing a probe includes the method for amplifying the trace amount of mRNA.

According to the arrangement, even if the initial amount of the mRNA is trace, the mRNA can be efficiently amplified. Thus, it is possible to prepare a probe from the trace amount of the mRNA.

In order to attain the object, a stepwise subtraction technique of the present invention includes the method for amplifying the trace amount of mRNA.

According to the arrangement, even if the initial amount of the mRNA is trace, the mRNA can be efficiently amplified. Thus, it is possible to carry out stepwise subtraction with the trace amount of the mRNA.

For a fuller understanding of the nature and advantages of the invention, reference should be made to the ensuing detailed description taken in conjunction with the accompanying drawings.

BRIEF DESCRIPTION OF DRAWINGS

FIG. 1(a) is an explanatory drawing illustrating a feature of the present invention.

FIG. 1(b) is an explanatory drawing illustrating a feature of the present invention.

FIG. 2 illustrates an embodiment of the present invention, and is a flow chart showing steps of a method for amplifying a trace amount of mRNA of the present invention.

BEST MODE FOR CARRYING OUT THE INVENTION

Figure 3:
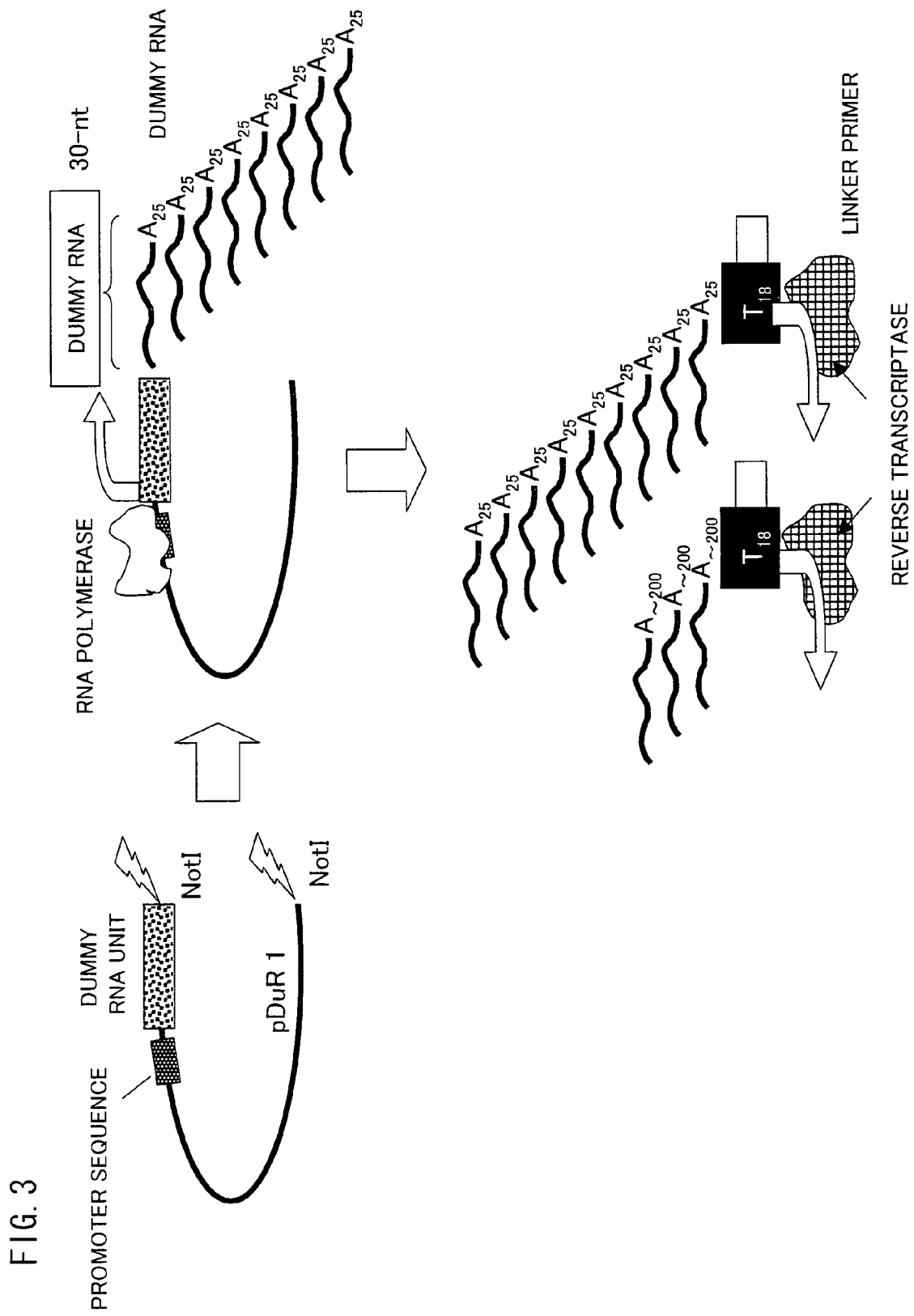
FIG. 3 illustrates an embodiment of the present invention, and is an explanatory view illustrating a method for preparation of a dummy RNA.

One embodiment of the present invention is described below with reference to FIGS. 1(*a*), 1(*b*), 2, and 5. Firstly, the following description explains briefly about a basic principle of the present invention, in comparison with a conventional technique.

*31 As described above, RNA amplification is conventionally carried out by a method for amplifying an RNA by use of (i) a double strand DNA for amplification in which a promoter sequence of RNA polymerase is ligated and (ii) the RNA polymerase. However, although the conventional method is capable of amplifying the RNA in a case where there is a large amount of the double strand DNA for amplification, the conventional method cannot amplify the RNA if there is only a small amount of the double strand DNA for amplification.

A reason why the RNA cannot be amplified conventionally when there is only a small amount of the double strand DNA can be easily understood from Michaelis-Menten equation. That is, an optimum substrate concentration of an enzyme used in cDNA library preparation, such as the RNA polymerase, is known to be in the order of millimoles (mM). The optimum substrate concentration (Michaelis constant: $K_m$) is obtained from the Michaelis-Menten equation (see Formula (I)). In the Formula (I), $K_m=(K2+K3)/K1$; $V_{max}$ is a maximum reaction rate, and [S] is the substrate concentration.

$$V=V_{max}[S]/(K_m+[S]) \quad (I)$$

When $[S]=K_m$, $V=V_{max}/2$, where $V_{max}$ is a reaction rate at a time when all enzymes generate a complex with the substrate. It is understandable from the Formula (I) that in a case where the [S] is extremely small in amount, the enzyme reaction hardly proceeds. Note that the [S] in the Formula (I) is a concentration of the double-strand DNA for amplification, and the enzyme whose reaction rate is calculated in the Formula (I) is the RNA polymerase.

Accordingly, in the conventional method as in Patent Document 1, the foregoing problem is solved by amplifying the double strand DNA for amplification by PCR, then subsequently amplifying a trace amount of mRNA by causing the double strand DNA for amplification to react with the RNA polymerase.

However, in the method that uses PCR, it is not possible to amplify the short mRNA and the long mRNA at a same efficiency level. The following description explains this in detail with reference to FIG. 1(*a*). FIG. 1(*a*) illustrates PCR which uses a double strand DNA for amplification that has three types of lengths as templates, and causes this double strand DNA for amplification to react with a DNA polymerase. In such PCR, a longest template is amplified once, a next longest template is amplified three times, and a shortest template is amplified six times, each in a predetermined time. Hence, the double strand DNA for amplification that is amplified by the PCR results in having many of the short double strand DNA, and few of the long double DNA. If the mRNA is prepared with the RNA polymerase from the double strand DNA for amplification that is amplified in a quantitatively unbalanced manner due to the difference in length of the sequence, there is a disadvantage that the mRNA obtained as a result would also have many of the short mRNA and few of the long mRNA.

On the other hand, in the present invention, the double strand DNA for amplification is prepared in such a manner that, in advance, the dummy RNA is mixed in with the mRNA that is to be amplified. As a result, a reaction rate of a reverse transcriptase is increased even in the case where the mRNA usable for amplification is few in amount, thereby allowing the double strand DNA for amplification to be effectively synthesized. More specifically, in a method for amplifying the trace amount of mRNA of the present invention, the dummy RNA is added to the trace amount of the mRNA in advance, so that an entire amount of the RNA is increased. This increases an apparent substrate concentration (Michaelis constant: $K_m$). The double strand DNA for amplification is prepared by use of this substrate RNA, so that the amount of the double strand DNA for amplification prepared as a result is adjusted to an optimum substrate concentration of the RNA polymerase. Consequently, the transcription reaction can proceed with a small amount of the mRNA, even though transcription reaction cannot proceed with such an amount of the mRNA without the above arrangement.

Moreover, the method of the present invention for amplifying the trace amount of mRNA does not require the use of PCR as a preliminary step of amplifying the mRNA by the RNA polymerase. Therefore, regardless of the length of the base sequence, it is possible to amplify the short mRNA and the long mRNA at a same efficiency level. The following description explains this point with reference to FIG. 1(*b*). FIG. 1(*b*) illustrates a step of amplifying an RNA by use of an RNA polymerase. In FIG. 1(*b*), a double strand DNA for amplification which has three types of lengths as templates is used, and the RNA is amplified by reacting the double strand DNA for amplification with the RNA polymerase. In this case, the longest template is amplified six times, the next longest template is also amplified six times, and the shortest template is also amplified six times, each in a predetermined time. That is to say, in the method for amplifying the mRNA according to the present invention, the number of times the amplification is carried out per unit time is not dependent on the length of the double strand DNA for amplification. Thus, it is possible to amplify the short mRNA and the long mRNA at a same efficiency level.

As described above, the method for amplifying the trace amount of mRNA of the present invention is a revolutionary method which is based on a principle completely different from that of the conventional method for amplifying the mRNA, and which can amplify the short mRNA and long mRNA at a same efficiency level regardless of how long the base sequence is. The following description describes in detail of steps of the method for amplifying the trace amount of mRNA according to the present invention.

[Method for Amplifying a Trace Amount of mRNA]

The method for amplifying a trace amount of mRNA of the present invention is not limited, as long as the method includes the following steps: (i) adding a dummy RNA to a solution which contains the trace amount of mRNA, so as to prepare a mixed solution; (ii) synthesizing an anti-sense DNA by reverse transcription which uses the mixed solution as a template; (iii) synthesizing a sense DNA which is complementary to the anti-sense DNA thus synthesized, so as to generate a double strand DNA made of the sense DNA and anti-sense DNA; (iv) ligating an RNA polymerase promoter sequence to the double strand DNA thus generated, on a sense DNA 5' end side of the double strand DNA, so as to prepare a double strand DNA for amplification; and (v) amplifying, by using RNA polymerase, an RNA from the double strand DNA for amplification. Specific arrangements such as other material, steps, conditions, equipment to be used and the like are not particularly limited. The following description explains each of the steps in detail.

<Step (i)>

A step (i) is a step in which a dummy RNA is added to a solution which contains the trace amount of mRNA, so as to prepare a mixed solution.

The "trace" of the "trace amount of mRNA" indicates such an amount of an mRNA that the synthesis of the double strand DNA from the mRNA will have an extremely slow transcription reaction in the latter step (v) with a RNA polymerase and the double strand DNA for amplification as the template. Moreover, it is easily understandable from the present specification that even in a case where the amount of mRNA is so relatively great that the RNA polymerization can proceed, the transcription reaction rate is further increased by use of the dummy RNA.

The "dummy RNA" in the present specification denotes such a RNA which the addition of the dummy DNA to the RNA to be amplified allows at least the reverse transcription and the ligase reaction to work with a greater amount of RNA that is to be a substrate of a reverse transcriptase and an amount of DNA that is to be a substrate of ligase.

The mRNA may be one which is purified from a cell or tissue of such as an animal, a plant, or a microorganism. Alternatively, the mRNA may be one which is synthesized. As such, there are no particular limitations to the mRNA. A purifying method of the trace amount of the mRNA is also not particularly limited, and may be purified by use of a well known method, as appropriate.

The dummy RNA is not particularly limited in terms of its sequence, however the dummy RNA preferably contains a poly(A) sequence. The presence of the poly(A) sequence in the dummy RNA enables the mRNA and the dummy RNA to be reverse-transcribed by use of a same primer. An example of the primer is, for example, an oligo-dT primer.

The poly(A) sequence may have any length, provided that the poly(A) sequence of the length can be specifically annealed and reverse-transcribed by the oligo-dT primer. For example, the poly(A) sequence is preferably made of at least 18 adenylic acids.

Further specifically, the sequence of the dummy RNA is preferably the base sequence shown in SEQ ID No. 4, 6, or 16. As described above, the dummy RNA having the poly(A) sequence and the trace amount of the mRNA can be simultaneously reverse-transcribed by use of a same primer which contains the oligo-dT sequence.

Preparation of the dummy RNA is not limited to a specific method, and can be performed with a well known method as appropriate. For example, the dummy RNA may be prepared by expressing the dummy RNA from a vector into which a double strand DNA containing the sequence of the dummy RNA is inserted. The method of preparing the dummy RNA by use of the vector can prepare the dummy RNA as many times as desired, once the vector is generated. Thus, this method advantages in that a large amount of dummy RNA can be prepared at low cost. More specifically, a sense DNA which encodes the base sequence of the dummy RNA and an anti-sense DNA are synthesized, and these sense DNA and anti-sense DNA are subsequently annealed so as to generate a double strand DNA. Thereafter, this double strand DNA is inserted into an expression vector or the like and transcribed by a well known RNA polymerase. Thus, the dummy RNA is prepared. The expression vector is not particularly limited as long as the expression vector includes the RNA polymerase promoter sequence so that an RNA can be transcribed from the inserted double strand DNA.

The dummy RNA may also be synthesized and prepared by a well known method. Although the method which prepares the dummy RNA by synthesis costs more as compared to the method of preparing the dummy RNA by use of the vector, the method which prepares the dummy RNA by synthesis is advantageous in that various chemical modification may be carried out to the dummy RNA, such as biotinylation. For example, the biotinylation of the dummy RNA allows such dummy RNA to specifically bind with streptavidin. That is to say, the dummy RNA can be removed specifically from a reaction mixture by a biotin streptavidin method.

It is preferable for the dummy RNA to be biotinylated. The biotinylation of the dummy RNA enables specific removal of just the dummy RNA from the reaction solution by the biotin streptavidin method. The method for biotinylating the dummy RNA is not particularly limited, and a well known method can be used as appropriate.

It is preferable that a concentration of the dummy RNA in the mixed solution be in a range of 0.5 to 10 μg/μL. Moreover, the concentration of the dummy RNA in the mixed solution is more preferably in a range of 0.5 to 2.5 μg/μL, and is most preferably 1 μg/μL. This preferable concentration range is a concentration range which were uniquely determined as a result of diligent studies through later-described Examples by the inventors. By having the concentration of the dummy RNA be the foregoing concentration, an entire RNA amount in the mixed solution can be prepared in the order of millimoles (mM). As a result, the double strand DNA for amplification that is prepared from this mixed solution also has a concentration in the order of millimoles (mM). The optimum substrate concentration of the RNA polymerase is in the order of millimoles (mM), likewise. As a result, it is possible to efficiently proceed a transcription reaction which, without the above arrangement, should be difficult to proceed due to a small amount of the double strand DNA for amplification.

A solvent of the mixed solution containing the trace amount of mRNA and the dummy RNA is not limited as long as the solvent does not inhibit the reverse-transcription in the later step. For example, suitable material that is used as a buffer solution such as Tris-HCl, or water is used as appropriate.

<Step (ii)>

A step (ii) is a step of synthesizing an anti-sense DNA by the reverse transcription which uses the mixed solution as a template.

Step 1 in FIG. 2 schematically illustrates the present step (ii). In the present step (ii), as illustrated in Step 1 in FIG. 2, an anti-sense DNA of the trace amount of the mRNA and the dummy RNA is synthesized by the reverse transcription which uses the trace amount of the mRNA and the dummy RNA in the mixed solution as the template. The step (ii) can use any reverse transcriptase, and may employ a well known reverse transcriptase as appropriate.

The primer is not particularly limited as long as the primer is capable of annealing the trace amount of the mRNA and the dummy RNA. However, in a case where both the trace amount of the mRNA and the dummy RNA have the poly(A) sequence, it is preferable to use an oligo-dT primer. The oligo-dT primer is capable of performing the simultaneous reverse transcription of both the trace amount of the mRNA and the dummy RNA, and as a result, allows simpler operations and lower costs.

<Step (iii)>

A step (iii) is a step of synthesizing a complementary sense DNA corresponding to the anti-sense DNA synthesized in the step (ii), so as to generate a double strand DNA made of the sense DNA and the anti-sense DNA.

Step 2 in FIG. 2 schematically illustrates the present step (iii). In the present step (iii), as illustrated in Step 2 of FIG. 2, any DNA polymerase is applicable as long as the DNA polymerase is capable of synthesizing the complementary sense DNA corresponding to the anti-sense DNA, and a well known DNA polymerase can be used as appropriate.

As a preliminary step before the synthesis of the sense DNA by the DNA polymerase, a degradation step of the dummy RNA and the trace amount of mRNA by use of Rnase is preferably included in the step (iii), the dummy RNA and the trace amount of mRNA having been used as the templates in the synthesis of the anti-sense DNA in the step (ii). The RNase is not particularly limited as long as the RNase is capable of degrading the trace amount of the mRNA and the dummy RNA. For example, RNase H may be used as the RNase.

<Step (iv)>

A step (iv) is a step of ligating an RNA polymerase promoter sequence to the double strand DNA thus generated in the step (iii), on a sense DNA 5' end side of the double strand DNA, so as to prepare a double strand DNA for amplification.

The step (iv) is not particularly limited in how the RNA polymerase promoter sequence is ligated, as long as the RNA polymerase promoter sequence is ligated to the double strand DNA generated in the step (iii) on just the sense DNA 5' end side as a result.

For example, it is preferable for the step (iv) to include a step (vi) in which an amplification adaptor containing the RNA polymerase promoter sequence is ligated to both ends of the double strand DNA generated in the step (iii) and subsequently the amplification adaptor that is ligated to the double strand DNA on a sense DNA 3' end side is cleaved off. How to cleave off the amplification adaptor ligated to the double strand DNA on the sense DNA 3' end side is not particularly limited, however it is preferable to cleave off the amplification adaptor by use of a restriction enzyme. In a case where the amplification adaptor is to be cut off by use of the restriction enzyme, it is preferable to generate a restriction enzyme site on the double strand DNA on the sense DNA 3' end side of the double strand DNA at a time when the promoter sequence is ligated to both the ends of the double strand DNA generated in the step (iii), so that just the promoter sequence ligated to the double strand DNA on the sense DNA 3' end side is to be cleaved off. The restriction enzyme is not particularly limited as long as the restriction enzyme does not exist on the sense DNA 5' end side of the double strand DNA. In addition, it is preferable for the restriction enzyme site to be incorporated in oligo-dT primer.

Step 3 in FIG. 2 schematically illustrates the present step (vi). In Step 3, amplification adaptors which contain the RNA polymerase promoter sequence are ligated to both ends of the double strand DNA generated in Step 2, respectively. Meanwhile, the oligo-dT primer is prepared so as to generate a NotI site on the sense DNA 3' end side just when the amplification adaptor is ligated to the double strand DNA on the sense DNA 3' end side. Thus, by processing the double strand DNA ligated to the amplification adaptor by NotI, it is possible to cleave the amplification adaptor off from the double strand DNA on the sense DNA 3' end side. The step (iv) may also be arranged such that just the amplification adaptor that is ligated to the double strand DNA on the sense DNA 5' end side is to be cleaved off. As such, by cleaving off one of the ligated amplification adaptor, it is possible to selectively amplify just the sense RNA or just the anti-sense RNA.

Moreover, it is preferable for the step (iv) to include a step (vii) in which the amplification adaptor thus cleaved off and the dummy RNA are removed. Due to the removal of the amplification adaptor thus cleaved off and the dummy RNA in the step (vii), the RNA amplification by use of the RNA polymerase in the latter step (v) can be carried out in such a manner that the RNA polymerase will bind only to the double strand DNA on the sense DNA 5' end side, but will not bind to the amplification adaptor thus cleaved off and the dummy RNA. Hence, the trace amount of the mRNA and the dummy RNA are transcribed efficiently, and various noises that tend to be readily generated in the amplification step of the trace amount of mRNA are reduced.

The step (vii) is not particularly limited as long as the amplification adaptor thus cleaved off and the dummy RNA can be removed thereby. For example, a size fractionation technique by use of a gel filtration column may be used as the step (vii). The gel filtration column is not particularly limited, and a well known column can be used as appropriate, considering which size is to be fractionated. The use of the size fractionation technique with the gel filtration column enables removal of both the amplification adaptor thus cleaved off and the dummy RNA, simultaneously. In a case where the dummy RNA is biotinylated, the step (vii) may include a dummy RNA removal step by use of a biotin streptavidin method or the like. Biotin is known of its specific binding to streptavidin. Therefore, a biotinylated dummy RNA is specifically removed by passing the reaction solution through a streptavidin column or the like.

The amplification adaptor contains the RNA polymerase promoter sequence. A promoter sequence is not particularly limited as long as the RNA polymerase is bindable thereto, and is capable of transcribing a base sequence positioned downstream of the promoter sequence. For example, the promoter sequence may be, but not limited to, a base sequence including a T7 promoter sequence, a T3 promoter sequence, or an SP6 promoter sequence. The base sequences of each of the promoter sequences are specifically:

```
T7 promoter sequence:
5'-TAATACGACTCACTATAGGGAGA-3';      (SEQ ID No. 1)

T3 promoter sequence:
5'-AATTAACCCTCACTAAAGGG-3';         (SEQ ID No. 2)
and

SP6 promoter sequence:
5'-ATTTAGGTGACACTATAGAATAC-3'.      (SEQ ID No. 3)
```

In a case where the promoter sequence is ligated to a double strand DNA, it is preferable to generate an amplification adaptor by annealing (i) a sequence containing the promoter sequence and (ii) a complementary strand DNA of the sequence, and subsequently ligating the amplification adaptor thus generated to the double strand DNA. How the promoter sequence and the complementary DNA strand of the promoter sequence are prepared is not particularly limited, and a well known method can be adopted to perform the synthesis.

Moreover, in a case where the amplification adaptor is to be ligated to the double strand DNA, it is preferable to ligate the amplification adaptor and the double strand DNA by use of a DNA ligase. The DNA ligase is not particularly limited as long as the DNA ligase is capable of ligating the amplification adaptor to the double strand DNA.

<Step (v)>

The step (v) is a step in which RNA is amplified from the double strand DNA for amplification, by the RNA polymerase.

As illustrated in Step 4 of FIG. 2, the step (v) is a step in which the trace amount of mRNA and the dummy RNA are amplified by use of the RNA polymerase and the double strand DNA for amplification generated in the step (iv). The RNA polymerase is not particularly limited, as long as the RNA polymerase is bindable to a promoter sequence in the amplification adaptor ligated to the double strand DNA for amplification, and is capable of transcribing RNA from a DNA positioned downstream of the promoter sequence. For example, it is preferable for the RNA polymerase to be T7 polymerase, T3 polymerase, or SP6 polymerase. Moreover, it is preferable to use, as the promoter sequence, a promoter sequence which is capable of receiving transcription regulation by each of the RNA polymerase.

[Method for Preparing a cDNA Library]

As long as the method of the present invention for amplifying the trace amount of mRNA is contained as one step, a cDNA library may be prepared in any method in the present invention, and other specific arrangements such as material, steps, conditions, used equipment or the like are not particularly limited.

More specifically, it is preferable for a method of the present invention for preparing the cDNA library to include a step in which (i) a double strand DNA is prepared from an amplified mRNA obtained by the method of the present invention for amplifying the trace amount of mRNA, and (ii) subsequently such obtained double strand DNA is inserted into a vector. This preparation method is also not particularly limited, and the preparation can be carried out by use of a well known method as appropriate (for example, see "Biomanual series 2, How to make a gene library (*Biomanual series 2, Gene library no sakuseihou*)" edited by Nojima, H. (1994), published by Youdo sha; or "Basic Biochemical Experiment Methods (*Kisoseikagakujikkenhou*), Vol. 4, Nucleic Acid/Gene Experiment II," edited by Ooshima, Y. (2000), published by Tokyo Kagaku Dojin).

Figure 4:
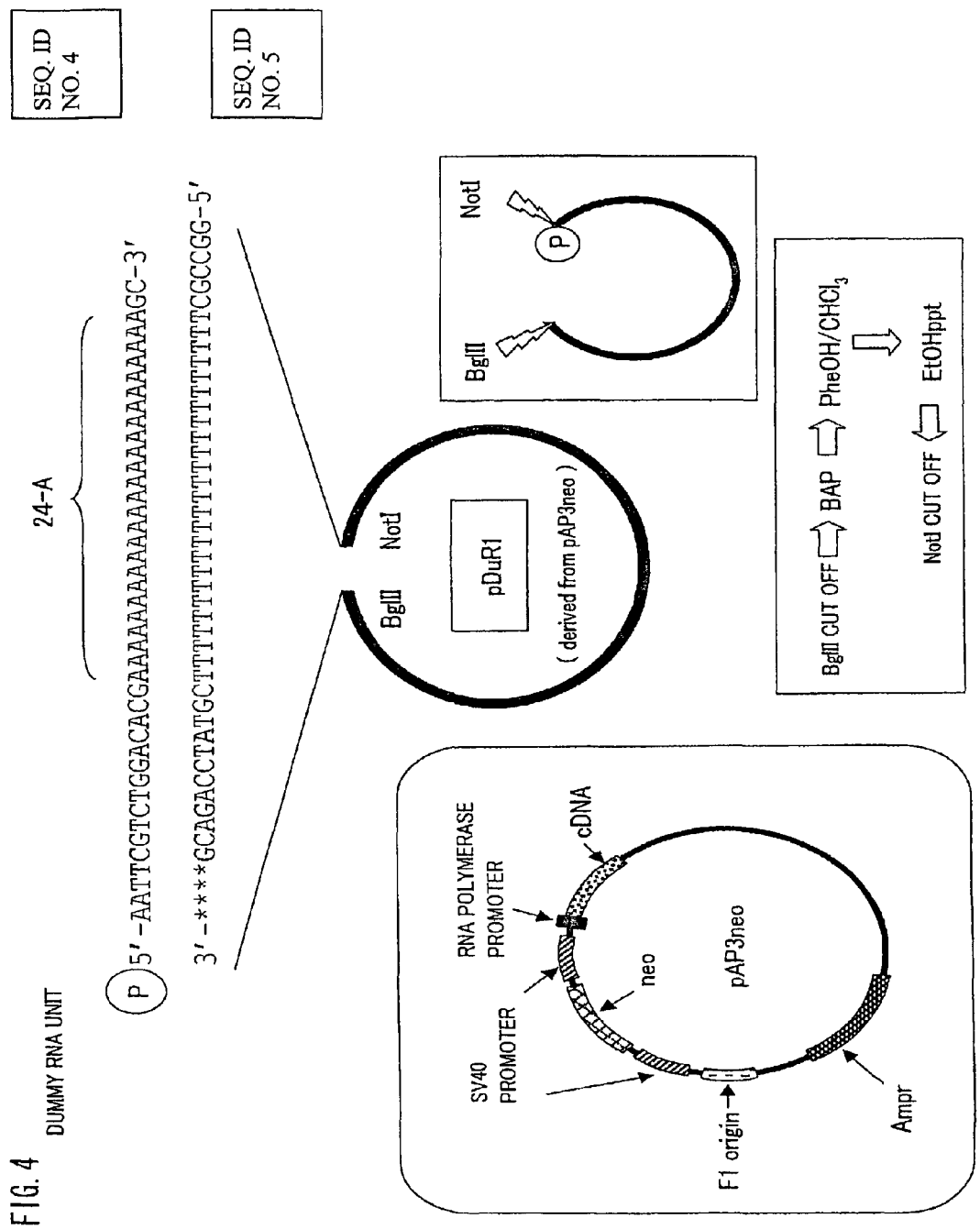
FIG. 4 illustrates an embodiment of the present invention, and is a flow chart showing steps of a method according to the present invention for preparing a cDNA library.

One example of how to prepare the cDNA library of the present invention is schematically illustrated in FIG. 4. Note that the present invention is not limited to the following description.

Figure 5:
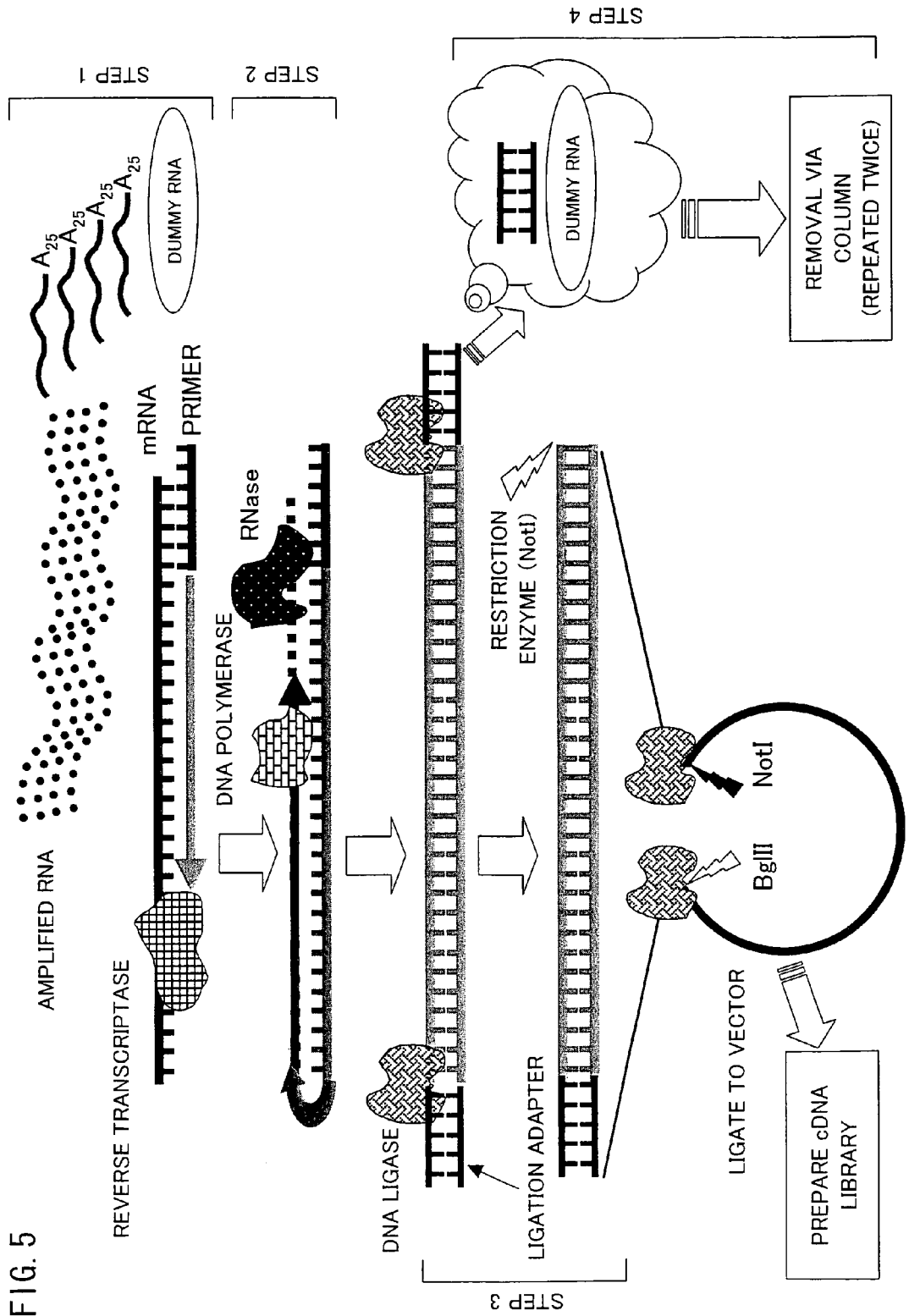
FIG. 5 is a schematic view of a vector for preparation of a dummy RNA prepared in Examples.

Step 1 of FIG. 5 is a step in which an anti-sense DNA is synthesized by reverse transcription in which the mRNA amplified in the step (v) according to the present invention for amplifying the trace amount of mRNA is used as a template. A method of this Step 1 is in accordance with the method in the step (ii) of the method of the present invention for amplifying the trace amount of mRNA. Note that the mRNA that is to be amplified in the step (v) contains the amplified trace amount of mRNA and the amplified dummy RNA.

Step 2 of FIG. 5 is a step of synthesizing a sense DNA that is complementary to the anti-sense DNA synthesized in Step 1, so as to generate a double strand DNA that is made of the sense DNA and the anti-sense DNA. This method is in accordance with the method of the step (iii) of the method of the present invention for amplifying the trace amount of mRNA.

Step 3 of FIG. 5 is a step for ligating, by use of a DNA ligase, a ligation adaptor to the double strand DNA generated in Step 2, on the sense DNA 5' end side of the double strand DNA. The DNA ligase is not particularly limited as long as the DNA ligase is capable of ligating the ligation adaptor to both ends of the double strand DNA.

The ligation adaptor is not particularly limited as long as the ligation adaptor can be ligated to both ends of the double strand DNA. It is preferable for the base sequence of the oligo-dT primer to have a base sequence in which just one of the ligation adapters can be cleaved off by a restriction enzyme in a case where the ligation adaptor is ligated to both ends of the double strand DNA. The restriction enzyme is not particularly limited. For example, Step 3 of FIG. 5 illustrates a case where the restriction enzyme is NotI. Moreover, it is preferable for the ligation adaptor to be arranged such that a side of the ligation adaptor that is not ligated to the double strand DNA is prepared so as to be a restriction enzyme site. The restriction enzyme site is not particularly limited. For example, Step 3 of FIG. 5 illustrates an example in which the restriction enzyme site is a BglII site. As a result of this arrangement, the ends of the double strand DNA which has been processed by the NotI in Step 3 have the BglII site and the NotI site, respectively. Thus, insertion into a vector is easily carried out.

It is preferable to include Step 4 for removing the ligation adaptor thus cleaved off and the amplified dummy RNA, subsequent to Step 3. Step 4 is not particularly limited, as long as the ligation adaptor thus cleaved off and the amplified dummy RNA can be removed thereby. For example, the size fractionation technique using the gel filtration column may be used as Step 4. The gel filtration column is not particularly limited, and a well known column may be used as appropriate depending on which size is to be fractioned. Moreover, it is preferable to carry out Step 4 several times. Carrying out of Step 4 several times further efficiently removes the ligation adaptor thus cleaved off and the amplified dummy RNA.

The double strand DNA that is purified through Steps 1 through 4 is inserted into a vector by use of the DNA ligase. Thus, the cDNA library is prepared. The vector is not particularly limited, and a well known vector is used as appropriate. For example, known vectors such as a plasmid vector, a cosmid vector, or a phage vector may be used.

[Method for Preparing Probe]

As long as the method of the present invention for amplifying the trace amount of mRNA is contained as one step, a probe may be prepared in any method in the present invention, and other specific arrangements such as material, steps, conditions, used equipment or the like are not particularly limited.

More specifically, the method of the present invention for preparing the probe is one which prepares a probe by use of an mRNA that is amplified by the method of the present invention for amplifying the mRNA. The "probe" in the present specification denotes an RNA probe and a DNA probe. How to prepare the RNA probe or the DNA probe from the mRNA is not particularly limited, and the preparation can be carried out in a well known method (For example, see "Biomanual series 2, How to make a gene library" (*Biomanual series 2, Gene library no sakuseihou*) edited by Nojima, H. (1994), published by Youdo sha; or "Basic Biochemical Experiment Methods (*Kisoseikagakujikkenhou*) Vol. 4, Nucleic Acid/Gene Experiment II", edited by Ooshima, Y. (2000), published by Tokyo Kagaku Dojin).

The method of the invention of the present application for preparing the probe can prepare, for example, a probe for a cDNA microarray.

[Stepwise Subtraction Technique]

A stepwise subtraction technique of the present invention at least includes the method of the present invention for amplifying the trace amount of mRNA, and is not particularly limited in other specific arrangements such as materials, steps, conditions, used equipment or the like.

More specifically, the stepwise subtraction technique of the present invention is a stepwise subtraction technique that examines the mRNA amplified by the method of the present invention for amplifying the trace amount of mRNA. The stepwise subtraction technique is not particularly limited, and may be carried out according to a well known method (For example, see "Biomanual series 2, How to make a gene library (*Biomanual series 2, Gene library no sakuseihou*)" edited by Nojima, H. (1994), published by Youdo sha; or "Basic Biochemical Experiment Methods (*Kisoseikagakujikkenhou*) Vol. 4, Nucleic Acid/Gene Experiment II", edited by Ooshima, Y. (2000), published by Tokyo Kagaku Dojin).

EXAMPLES

The following description explains the present invention in more details with reference to Examples, however the present invention is not limited to this. Various modifications, corrections, and alterations may be made within the scope of the present invention by a person skilled in the art.

[1: Preparation of Vector for Preparation of Dummy RNA]

A method of the present invention for preparing a vector for preparation of a dummy RNA is described below with reference to FIG. 4.

First, a sense strand (Sense) and an anti-sense strand (Antisense) were annealed so as to prepare a dummy RNA unit. In order to prepare the dummy RNA unit, each of the sense strand (Sense) and the anti-sense strand (Antisense) was synthesized, and a 5' end of the sense strand was phosphorylated, so that the dummy RNA unit could be inserted into a vector. The following shows the base sequences of the sense strand and the anti-sense strand:

```
Sense:
                                        (SEQ ID No. 4)
5'-AATTCGTCTGGACACGAAAAAAAAAAAAAAAAAAAAAAAAAGC-3'

Antisense:
                                        (SEQ ID No. 5)
5'-GGCCGCTTTTTTTTTTTTTTTTTTTTTTTTTCGTATCCAGACG-3'
```

The sense strand and the anti-sense strand were dissolved in an annealing buffer (10 mM Tris-HCl (pH 7.5), 1 mM EDTA, 10 mM $MgCl_2$) in such a manner that the sense and anti-sense strands were in equal concentration and totally 0.35 μg/μL in the annealing buffer. Thereafter, the mixture was kept at 65° C. for 2 minutes, at 37° C. for 10 minutes, and at room temperature for 5 minutes, so that the sense strand and the anti-sense strand annealed. In this way, a dummy RNA unit was prepared. Note that an EcoRI site and a NotI site were generated on both edges of the dummy RNA unit, respectively. This allows insertion of the dummy RNA unit into an expression vector by use of the restriction enzyme sites.

Subsequently, a vector into which the dummy RNA unit was to be inserted was prepared. As the vector, pAP3neo (produced by Takara Bio) was used. The pAP3neo was cleaved off by the EcoRI and the NotI, and was subjected to electrophoresis in agarose gel. Further, the pAP3neo was purified from the agarose gel. The pAP3neo was inserted with the dummy RNA cassette, as a result of which the vector for producing the dummy RNA (pDurin-1) was prepared.

[2: Preparation of Dummy RNA]

A method for producing the dummy RNA by use of the pDurin-1 follows (1) through (11) below. FIG. 3 schematically illustrates a method for preparing the dummy RNA by use of the pDurin-1.

(1) 20 μL of 10× NotI Buffer (100 mM Tris-HCl (pH7.5), 1.5M NaCl, 70 mM $MgCl_2$, 10 mM DTT, 0.1% BSA, 0.1% Triton X-100) was added to 10 μg of pDurin-1, and further water was added thereto so that an entire amount reached 200 μL.

(2) 5 units of NotI was added, and this mixture was kept at 37° C. for 2 hours. After the reaction, it was observed by agarose electrophoresis that the pDurin-1 was cut off.

(3) Phenol/chloroform solution (1:1) of a volume equal to the reaction liquid (210 μL) was added and stirred.

(4) The reaction liquid was centrifuged by a microfuge for 1 minute.

(5) Following the centrifugation, an obtained supernatant was transferred to a fresh microfuge tube. 3M sodium acetate of approximately 0.08 times the amount of the supernatant (17 μL) and ethanol of approximately twice an amount of the supernatant (420 μL) were added to the supernatant. Thereafter, the mixture was cooled in dry ice for 15 minutes.

(6) The mixture was centrifuged in the microfuge for 15 minutes. An obtained precipitation was lightly washed with 70% ethanol, and this was centrifuged for 2 seconds. A resultant supernatant was removed, and further a resultant precipitation was centrifuged for another 2 seconds. A small amount of 70% ethanol gathered in a bottom of the microtube was then removed therefrom. The process proceeded to the next stage without drying precipitation thus obtained, that is, with the precipitation kept wet.

(7) 20 μL of 10×T7 Pol Buffer (400 mM Tris-HCl (pH 8.0), 80 mM $MgCl_2$, 20 mM spermidin, 50 mM DTT) and 16 μL of 25 mM NTP mix were added to the precipitation containing the pDurin-1 cleaved off by the NotI. Further, water was added so that the entire amount reached 200 μL.

(8) 50 units (approximately 1 μL to 5 μL) of T7 RNA polymerase were added, and this mixture was kept at 37° C. for 60 minutes.

(9) Further, 5 units (approximately 1 μL) of DNase I (Rnase free) was added, and was kept at 37° C. for 20 minutes.

(10) The operations of (3) through (6) were carried out so as to obtain a precipitation.

(11) 100 μL of TE (10 mM Tris-HCl (pH 7.5), 0.1 mM EDTA) was added to the precipitation thus obtained and a concentration of the dummy RNA was measured by a UV meter. If a solution satisfies $OD_{260}$=1.0, the concentration of the dummy RNA in that solution is 40 μg/μL. After the concentration of the dummy RNA was measured, TE was added so that the concentration of the dummy RNA became 5 μg/μL. Thereafter, the dummy RNA was dispensed in a microfuge tube or the like, and was stored at −20° C. or −80° C. In this way, the dummy RNA was prepared by using the vector for preparing the dummy RNA.

As another method, a dummy RNA was prepared by chemical synthesis. In this case, the dummy RNA was chemically synthesized, and a 3' end of an obtained dummy RNA was biotinylated. This biotinylated dummy RNA was purified via HPLC. Such a biotinylated dummy RNA is also commercially available. The base sequence of the dummy RNA is shown as follows:

```
Dummy RNA:
                                        (SEQ ID No. 6)
5'-AATTCGTCTGGACACGAAAAAAAAAAAAAAAAAAAAAAAAA-3'
```

The dummy RNA thus synthesized was dissolved in water to reach a concentration of 1 μm/mL, and this liquid was stored at −20° C. or −80° C. Note that the following experiments used the biotinylated dummy RNA.

[3. Preparation of Double Strand DNA]

A Double strand DNA was prepared by following (1) through (10) described below:

(1) First, 0 µg, 0.5 µg, 1.0 µg, 2.5 µg, 5.0 µg or 10.0 µg of the dummy RNA were added to approximately 1 ng of a trace amount of mRNA (derived from approximately 100 cells) to be included in the library, and 5 mM Tris-HCl (pH 7.5) was added so that an entire amount reached 7.5 µL. Next, this mixture was heated at 65° C. for 5 minutes, and was cooled with ice. The trace amount of mRNA was obtained by a well known mRNA obtaining method. More specifically, the trace amount of mRNA was obtained by use of a QuickPrep Micro mRNA Purification Kit (Amersham Biosciences). Specific operations were carried out by following a protocol attached to the kit. An mRNA degradation caused by an RNase can be suppressed as much as possible, by addition of the dummy RNA at a time of mRNA extraction. In the present example, an mRNA purified from a 293T cell or from a HeLa cell was used as the trace amount of mRNA.

(2) The following were successively added in the mixture of the trace amount of mRNA and the dummy RNA: 2.5 µL of 10× First Strand Buffer (500 mM Tris-HCl (pH 8.3), 750 mM KCl, 30 mM $MgCl_2$), 2.5 µL of 0.1M DTT, 1.5 µL of 10× First Strand Mixture (10 mM dATP, 10 mM dGTP, 10 mM dTTP, 5 mM 5-methyl-dCTP), 1.0 µL (1.6 µg) of (T7) Linker Primer, and 0.5 µL (20 units) of RNase Inhibitor (produced by Promega). Thereafter, water was added so that an entire amount reached 25 µL. The following is a sequence of the (T7) Linker Primer. Note that the (T7) Linker Primer used was purified via HPLC.

```
(T7) Linker Primer:
                                          (SEQ ID No. 7)
5'-GAGAGAGAGAGAGAGATAATACGACTCACTATAGGGAGGCGGCCGCT

TTTTTTTTTTTTTTTTTT-3'
```

(3) The mixture was let stand at room temperature for 10 minutes so that the mRNA and the (T7) Linker Primer were annealed.

(4) 1 µL (50 units) of StrataScript RT (Stratagene cDNA Synthesis Kit, produced by Stratagene) and 0.5 µL of Superscript III (produced by Invitrogen) were added to the mixture, and was reacted at 42° C. for 45 minutes. Subsequently, 0.5 µL of SuperScript III was further added, and this mixture was reacted at 50° C. for 30 minutes. Thereafter, the mixture was further reacted at 55° C. 30 minutes.

(5) After termination of the reaction, the reaction solution was put in ice.

(6) Into the reaction solution thus cooled in ice, the following were added: 20 µL of 10× Second Strand Buffer (188 mM Tris-HCl (pH 8.3), 906 mM KCl, 46 mM $MgCl_2$), 7.5 µL of 0.1M DTT, and 3 µL of Second Strand Nucleotide Mixture (10 mM dATP, 10 mM dGTP, 10 mM dTTP, 25 mM dCTP). Thereafter, ice-cold water was added so that an entire amount reached 200 µL.

(7) Further, this mixture was cooled in ice for 5 minutes.

(8) 1.5 µL (2 units) of RNase H (produced by TaKaRa Bio) and 10 µL of *E. coli* DNA Polymerase I (produced by TaKaRa Bio) were added.

(9) This mixture was reacted at 16° C. for 150 minutes.

(10) After addition of 200 µL of phenol/chloroform solution with good stirring thereafter, this mixture was centrifuged (at a speed of 15,000 rpm for 3 minutes at 4° C.). After a supernatant was transferred to a fresh tube and ethanol precipitation (for at least 10 minutes at −80° C.) was carried out thereto, an obtained precipitation was washed with 70% ethanol. The obtained precipitation was not dried to be used in the following steps.

[4: Study Related to Optimum Amount of Dummy RNA]

It was studied how an amount of the dummy RNA in preparation of the double strand DNA affected a preparation efficiency of the double strand DNA.

*58 The obtained precipitation was dissolved in 85 mL of water, and 1 µL of this mixture was used as a template. To the template, 1 µL of 10 Ex Buffer, 0.8 µL of dNTP mix., 1 µL of each of the following primers (hsGAPDH-F and hsGAPDH-R), 0.1 µL of Ex taq, and 5.1 µL of water were added, so that an entire amount reached 10 µL. After denaturation at 95° C. for 5 minutes, the mixture was subjected to a PCR reaction of 30 to 50 cycles in which denaturation at 95° C. for 30 seconds, annealing at 55° C. for 30 seconds, and elongation at 72° C. for 1 minute were repeated. In a case where the trace amount of mRNA is obtained from approximately 1 cell, it is preferable that the PCR reaction is carried out by 50 cycles; in a case where the trace amount of mRNA is obtained from approximately 10 cells, the PCR reaction is preferably carried out by 40 cycles; and in a case where the trace amount of mRNA is obtained from approximately 100 cells, the PCR reaction is preferably carried out by 30 cycles.

```
                                          (SEQ ID No. 8)
    hsGAPDH-F: 5'-CGAGATCCCTCCAAAATCAA-3'

(SEQ ID No. 9)
    hsGAPDH-R: 5'-AGGGGTCTACATGGCAACTG-3'
```

Following the PCR reaction, electrophoresis was carried out with an obtained PCR reaction product (5 µL) by use of the 2% agarose gel. After the electrophoresis, fluorescent intensities of each of bands were measured by use of "Socion Image (NIH Image)". A result of this is explained in Result 1 later described.

[5: Study Related to Trace mRNA Amount]

The following samples were prepared: (i) a sample in which 1.0 µg of a dummy RNA was added to an mRNA (approximately 0.1 ng (equivalent to approximately 10 cells), or approximately 0.01 ng (equivalent to approximately 1 cell)) extracted from a 293T cell or a HeLa cell, and (ii) a sample in which a dummy RNA was not added.

A double strand DNA was prepared in the aforementioned method by use of the samples. An amplifiable amount of the trace amount of mRNA by the method of the invention of the present application for amplification was studied in the method described in [4. Study Related to Optimum Amount of Dummy RNA]. In a case where the trace amount of mRNA was 0.01 ng, the PCR reaction was carried out with 50 cycles, and in a case where the trace amount of mRNA was 0.1 ng, the PCR reaction was carried out with 40 cycles. A result of this is described in Result 2 later described.

[6: Preparation of Double Strand DNA for Amplification]

A double strand DNA for amplification was prepared by (1) through (13) described below:

(1) A sense strand and an anti-sense strand were synthesized for preparing an amplification adaptor. Note that the sense strand contains a T7 polymerase promoter sequence. Base sequences of the sense strand and the anti-sense strand are as follows:

Sense T7:
(SEQ ID No. 10)
5'-CACTAGTACGCGTAATACGACTCACTATAGGGAATTCCCCGGG-3'

Antisense T7:
(SEQ ID No. 11)
5'-CCCGGGGAATTCCCTATAGTGAGTCGTATTACGCGTACTAGTGAGCT-3'

The Sense T7 and the Antisense T7 were dissolved in an annealing buffer (10 mM Tris-HCl (pH 7.5), 1 mM EDTA, 10 mM MgCl$_2$) in such a manner that the Sense T7 and the Antisense T7 were in equal concentration and totally 0.35 µg/µL in the annealing buffer. Thereafter, the annealing buffer was kept at 65° C. for 2 minutes, at 37° C. for 10 minutes, and at room temperature for 5 minutes, so that the Sense T7 and the Antisense T7 were annealed. In this way, the amplification adaptor was prepared. The amplification adaptor was stored at −20° C.

(2) To the precipitation purified in [3: Preparation of Double Strand DNA], 10 µL of 10×T4 DNA Polymerase Buffer, 5 µL of 2.5 mM dNTP mixture, and water were added to reach 100 µL totally. 3.5 µL (approximately 5 units) of T4 DNA Polymerase was added to this solution, and was reacted at 37° C. for 30 minutes. Next, after 100 µL of phenol/chloroform solution was added and stirred, this solution was centrifuged. A resultant supernatant was transferred to a fresh tube so as to carry out ethanol precipitation (for not less than 10 minutes at −80° C.), then a precipitation thus obtained was washed with 70% ethanol. Carrying out of these steps obtained a blunt end double strand DNA.

(3) The following reagents were added to the blunt end double strand DNA (precipitation): 2 µL of 10× Ligase Buffer (500 mM Tris-HCl (pH 7.5), 70 mM MgCl$_2$, 10 mM DTT), 2 µL of 10 mM rATP, and 1 µL of the amplification adaptor (0.35 µg). Thereafter, water was added to reach 18.5 µL totally.

(4) After 1.5 µL (approximately 4 units) of T4 DNA Ligase was added, the mixture was reacted at 8° C. overnight.

(5) The mixture was heated at 70° C. for 30 minutes to inactivate the Ligase. Next, the mixture was centrifuged, and an obtained supernatant was purified.

(6) At this time, both ends of the double strand DNA that was purified as a precipitate in [3: Preparation of Double Strand DNA] were connected to amplification adaptors, respectively. In this case, if a T7 RNA Polymerase is reacted with the double strand DNA, not only the sense strand but also the anti-sense strand of the trace amount of mRNA are transcribed. In order to avoid this, NotI treatment was carried out, so that the amplification adaptor that controls transcription of the anti-sense strand of the trace amount of mRNA was removed. First, the following were added to the supernatant: 27 µL of NotI Buffer Supplement (278 mM NaCl, 8 mM MgCl$_2$, 1.8 mM DTT, 0.018% Triton X-100), and 3 µL of the NotI. Subsequently, this mixture was react at 37° C. for 90 minutes. After termination of the reaction, 5 µL of 10×STE and 2 µg of tRNA were added to the mixture. As such, the double strand DNA for amplifying the mRNA was prepared.

(7) Size fractionation was carried out for removing the amplification adaptor that had been cleaved off by a restriction enzyme. In the size fractionation, CHROMA SPIN-400 (produced by Clontech) was used. The CHROMA SPIN-400 was evenly suspended (by inverting a column so as to stir the content therein), and top and bottom lids of the column were removed. The CHROMA SPIN-400 was placed on an annex receptacle tube (or a 1.5 mL microfuge tube with its lid removed) for 10 minutes in order to drain out extra 1×TE (100 mM NaCl, 10 mM Tris-HCl (pH 8.0), 1 mM EDTA) that was contained in the column. Further, the CHROMA SPIN-400 and the 1.5 mL microfuge tube were set into a 15 mL plastic tube, and a low-speed centrifuge was carried out. The centrifuge was carried out by use of a low-speed centrifuge (Beckman J2-21), under a condition of a speed at 1800 rpm, for 3 minutes (700×g).

(8) After carrying out the low-speed centrifuge, a buffer that was spun down into the 1.5 mL microfuge tube was discarded, and again centrifuge was carried out at 1800 rpm for 3 minutes.

(9) After carrying out the low-speed centrifuge, the buffer that was spun down into the 1.5 mL microfuge tube was discarded.

(10) The CHROMA SPIN-400 was transferred to a fresh 1.5 mL microfuge tube, and 10 µL of the double strand DNA for amplification prepared in (6) was added on resin in a center of the CHROMA SPIN-400. The CHROMA SPIN-400 transferred to the fresh microfuge tube was set into a plastic tube of 15 mL, and was centrifuged by use of the low-speed centrifuge, under a condition of a speed at 1800 rpm for 5 minutes.

(11) 130 µL of TE, 20 µL of 5M NaCl, and an equal amount of phenol/chloroform solution were added to a sample (approximately 50 µL) spun down into the microfuge tube, and was stirred. Thereafter, the mixture was centrifuged for 2 minutes.

(12) An obtained supernatant was transferred to a fresh tube, and 400 µl of 100% ethanol was added. After stirring this mixture, the solution was stored at −80° C. for 10 minutes, or at −20° C. overnight.

(13) The supernatant was centrifuged at a speed of 15000 rpm at 4° C. for 10 minutes, and an obtained precipitation was collected. Thereafter, the obtained precipitation was washed with 70% ethanol.

Thus, the double strand DNA for amplification was prepared by the above steps.

[7: Removal of Dummy RNA]

(1) A precipitation obtained in [6: Preparation of Double Strand DNA for Amplification] was dissolved in water, and streptavidin was added to this solution. This solution was sufficiently stirred, and was let stand at room temperature for 5 minutes.

(2) A phenol/chloroform solution was added to this reaction solution and stirred, and an aqueous layer was collected from the reaction solution. The dummy RNA was removed by collecting the aqueous layer, since a dummy RNA/streptavidin complex transfers to the phenol/chloroform layer.

(3) TE was added to the phenol/chloroform layer thus remained in (2). This mixture was stirred and again an aqueous layer was collected.

(4) Streptavidin was added to the aqueous layers collected in steps (2) and (3), and steps (1) to (3) were repetitively carried out.

(5) A double strand DNA was purified from the collected aqueous layers by a minicent-30 filter (produced by Tosoh SMD) (MINICENT-30 (Cat. #08327)). Purification was carried out by following a method in an attached protocol.

[8: Preparation of cDNA Library]

Figure 14:
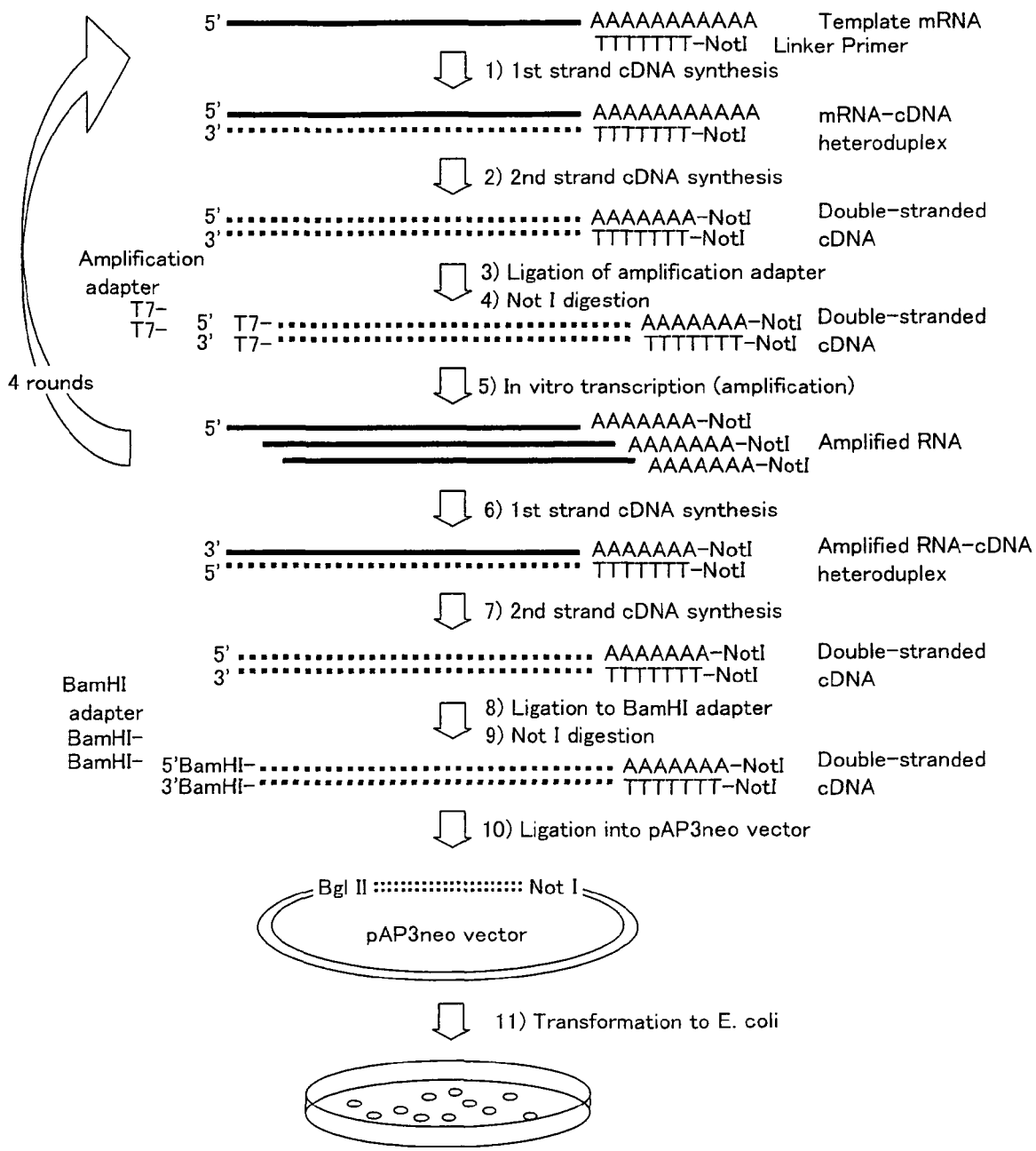
FIG. 14 is a flow chart showing steps for preparing a cDNA library in Examples.

FIG. 14 illustrates a preparation step of a cDNA library. The following description explains details of this step.

(1) 1 µL of dummy RNA (5 µg/µL), 10 µL of 10×T7 Pol Buffer, 8 µL of 25 mM NTP mix were added to a double strand DNA for amplification (precipitation) thus prepared, and water was added to reach a range of 95 µL to 99 µL totally.

(2) 50 units (approximately 1 to 5 μL) of T7 RNA polymerase were added to the solution, and the solution was let stand at 37° C. for 60 minutes.

(3) An excess of the amplified dummy RNA was removed by use of the CHROMA SPIN-400 in the aforementioned method. Amplified mRNA that remained after removal of the dummy RNA was ethanol-precipitated, and was collected as a precipitation. The present Example used this obtained mRNA in amplification of the mRNA, which mRNA was amplified by repetitively carrying out the steps of [3: Preparation of Double Strand DNA] through [8: Preparation of cDNA Library] four times. This amplified mRNA is used in the subsequent steps.

(4) 7.5 μL of 5 mM Tris-HCl (pH 7.5) was added to the mRNA thus collected in (3). This mixture was heated at 65° C. for 5 minutes, and then was cooled with ice.

(5) 2.5 μL of 10× First Strand Buffer, 2.5 μL of 0.1M DTT, 1.5 μL of 10× First Strand Mixture, 1.0 μL (1.6 μg) of (T7) Linker Primer (sequence number 7), and 0.5 μL (20 units) of RNase Inhibitor (Promega) were successively added to the solution. Subsequently, water was added to reach 25 μL totally.

(6) The solution was let stand at room temperature for 10 minutes, so that the mRNA and the (T7) Linker Primer were annealed.

(7) 1 μL (50 units) of StrataScript RT (Stratagene cDNA Synthesis Kit, Stratagene) and 0.5 μL of SuperScript III (Invitrogen) were added to the solution, and the solution was reacted at 42° C. for 45 minutes. Thereafter, a further 0.5 μL of SuperScript III was added, and the solution was reacted at 50° C. for 30 minutes. Subsequently, the solution was further reacted at 55° C. for 30 minutes.

(8) After termination of the reaction, the solution was placed in ice.

(9) 20 μL of 10× Second Strand Buffer, 7.5 μL of 0.1M DTT, and 3 μL of Second Strand Nucleotide Mixture were added to the solution in an ice-cooled state. Thereafter, ice-cold water was added to reach 200 μl totally.

(10) The solution was further cooled in ice for 5 minutes.

(11) 1.5 μL (2 units) of RNase H (produced by TaKaRa Bio) and 10 μL (50 units) of E. coli DNA Polymerase I (produced by TaKaRa Bio) were added to the solution.

(12) The solution was reacted at 16° C. for 150 minutes.

(13) 200 μL of phenol/chloroform solution was added to the solution and was stirred. Thereafter, the solution was centrifuged (at a speed of 15,000 rpm at 4° C. for 3 minutes). A supernatant obtained was transferred to a fresh tube and ethanol precipitation (at −80° C. for not less than 10 minutes) was carried out. An obtained precipitation was then washed with 70% ethanol.

(14) 10 μL of 10× T4 DNA Polymerase Buffer, 5 μL of 2.5 mM dNTP mixture, and water were added to the obtained precipitation to reach 100 μL totally. A further 3.5 μL (approximately 5 units) of T4 DNA Polymerase was added to this solution, and the solution was reacted at 37° C. for 30 minutes. Next, 100 μL of phenol/chloroform solution was added and stirred, and the mixture was centrifuged. Thereafter, a supernatant obtained was transferred to a fresh tube and ethanol precipitation (at −80° C. for not less than 10 minutes) was carried out. An obtained precipitation was washed with 70% ethanol. This step obtained a blunt end double strand DNA.

(15) 2 μL of 10× Ligase Buffer, 2 μL of 10 mM rATP, and two types of adaptors (entire amount of 1 μL, 0.35 μg) were added to the blunt end double strand DNA (precipitation), and subsequently water was added to reach 20 μL totally. One of the adaptors was an adaptor made of a double strand DNA containing a sequence in which a plurality of BamHI (BglII)-SmaI fragments as shown in the following sequence number 12 was ligated. The other adaptor was an adaptor made of a double strand DNA containing a sequence in which a plurality of SmaI fragments as shown in the following sequence number 13 was ligated.

```
                                      (SEQ ID No. 12)
BamHI (BglII)-SmaI fragment:   5'-GATCCCCGGG-3'

(SEQ ID No. 13)
SmaI fragment:                 5'-CCCGGG-3'
```

Note that a preparation method of the adaptors followed the preparation method of the amplification adaptor made of the Sense T7 and the Antisense T7.

(16) 1.5 μLl (approximately 4 units) of T4 DNA Ligase was added to the solution, and this solution was reacted at 8° C. overnight.

(17) The Ligase was denatured by heating the solution at 70° C. for 30 minutes. Thereafter, the solution was centrifuged for 5 seconds, which purified its supernatant.

(18) 27 μL of NotI Buffer Supplement and 3 μL of NotI were added to the solution, and this solution was reacted at 37° C. for 90 minutes. After the reaction was carried out, 5 μL of 10×STE and 2 μL of tRNA were added. Thereafter, a remaining dummy RNA and the like was removed in the aforementioned method by use of the CHROMA SPIN-400. The double strand DNA of which the dummy RNA and the like was removed, was ethanol-precipitated, and was collected as a precipitation.

(19) 3 μL of 10× Ligase Buffer, 3 μL of 10 mM rATP, and 1 μL (100 ng to 300 ng) of pAP3neo vector (cut off by NotI and BglII) were added to the precipitation, and water was thereafter added to reach 30 μL totally.

After 1 μL (4 units) of T4 DNA Ligase was added to the solution, the solution was reacted at 12° C. overnight.

(20) The solution was heated at 70° C. for 30 minutes.

(21) After the solution was heated, 70 μL of TE, and 100 μL of phenol/chloroform solution were added to the solution and stirred. Thereafter, the mixture was centrifuged at a speed of 15000 rpm for 1 minute. After the centrifuge, a supernatant thus obtained of 100 μL was collected. The supernatant was sterilized by use of a filter (UFCP3TK50, produced by Millipore).

(22) Escherichia coli (Electro MAX DH12S Cells, GIBCO-BRL) was transfected with the supernatant thus sterilized (5 μL) by an electroporation method. The electroporation method was carried out under a condition of 2.5 kv and 129 ohm. The E. coli to which voltage was applied was cultured at 37° C. for 1 hour in an SOC culture medium.

(23) The E. coli was transferred to an LB culture medium (containing ampicillin in a concentration of 50 mg/L) of 100 ml. The LB culture medium containing 10 μL or 100 μL of the E. coli was scattered on the LB culture medium (solid culture medium) containing the ampicillin, and was cultured at 37° C. overnight. Thereafter, a transformation efficiency of the E. coli was calculated. A remaining LB culture medium containing the E. coli was cultured at 37° C. for a few hours until $OD_{600}=1.0$ was reached. After culturing, DMSO was added to the LB culture medium containing the E. coli, and this solution was stored in a frozen state at −80° C.

Preparation of the library may also be possible by preparing a library with reference to a regular cDNA library preparation protocol (for example, see "Biomanual series 2, How to make a gene library (*Biomanual series 2, Gene library no sakuseihou*)" edited by Nojima, H. (1994), published by Youdo sha; or "Basic Biochemical Experiment Methods (*Ki-*

*soseikagakujikkenhou*) Vol. 4, Nucleic Acid/Gene Experiment II" edited by Ooshima, Y. (2000), Tokyo Kagaku Dojin). A result of the experiment is explained in Result 3 later described.

Result 1

Figure 6A:
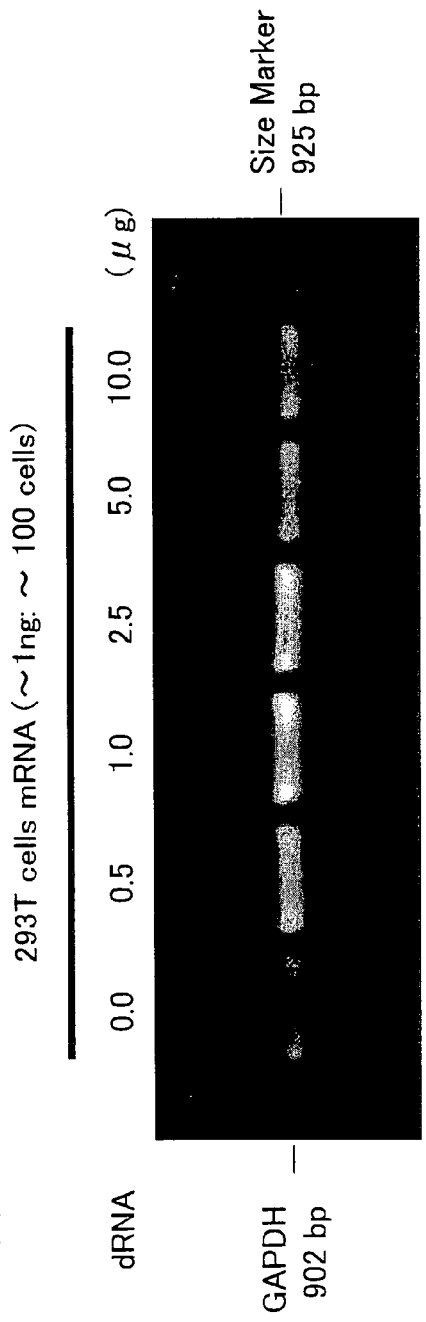
FIG. 6(a) is an electropherogram showing a result of determination of an optimal amount of a dummy RNA in Examples.
Figure 6B:
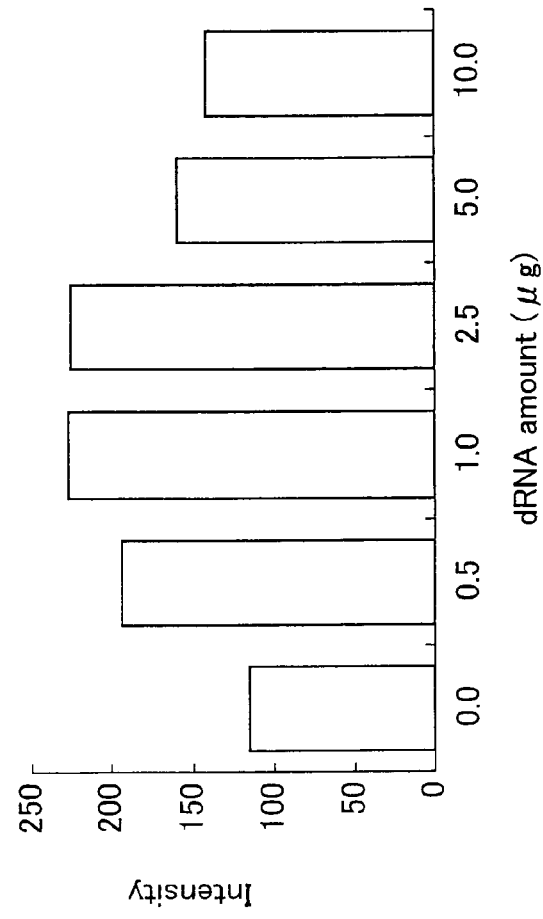
FIG. 6(b) is a graph showing a result of determination of an optimal amount of a dummy RNA in Examples.

FIGS. 6(*a*) and 6(*b*) show a result of an optimum amount of the dummy RNA. In the present invention, efficiency of converting GAPDH to cDNA is used as an index in studying an effect of the dummy RNA. However, GAPDH is simply one example of the index, and it is easily understandable to a person skilled in the art that the dummy DNA attains a same effect in conversion of another gene as the case of the GAPDH.

As shown in FIGS. 6(*a*) and 6(*b*), in a case where the dummy RNA of an amount of 0.5 µg, 1.0 µg, 2.5 µg, 5.0 µg, or 10.0 µg was added to a trace amount of mRNA (purified from approximately 100 cells) desirably included in a library of approximately 1 ng, it was demonstrated that the cDNA was efficiently synthesized as compared to not adding the dummy RNA, for all added amounts of the dummy RNA.

Moreover, as shown in FIGS. 6(*a*) and 6(*b*), a case where 1 µg of the dummy RNA is added to the trace amount of mRNA synthesized the cDNA most efficiently.

Result 2

Figure 7A:
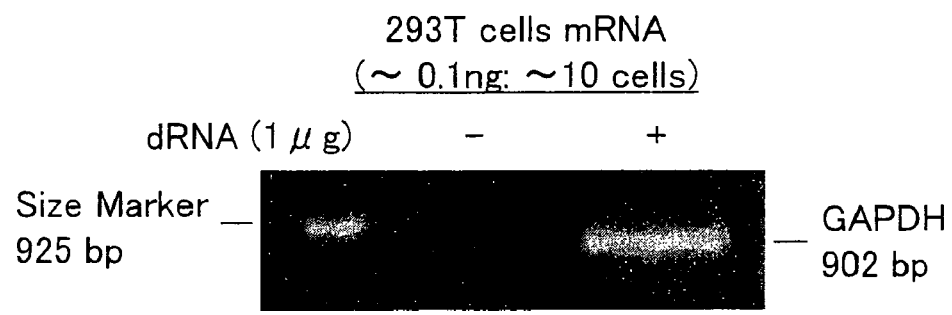
FIG. 7(a) is an electropherogram showing an amplifiable amount of a trace amount of mRNA in Examples.
Figure 7B:
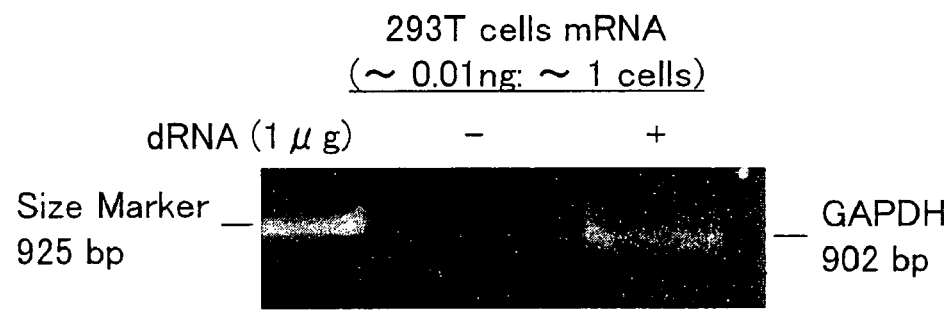
FIG. 7(b) is an electropherogram showing an amplifiable amount of a trace amount of mRNA in Examples.
Figure 7C:
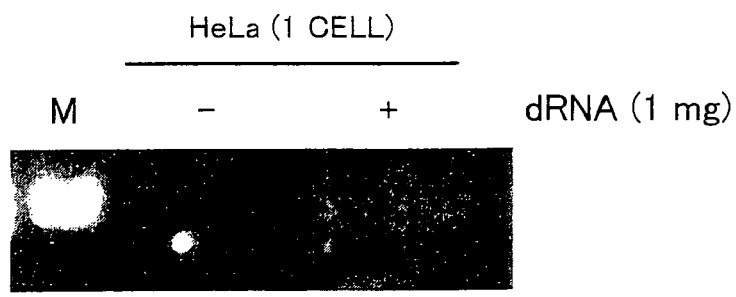
FIG. 7(c) is an electropherogram showing an amplifiable amount of a trace amount of mRNA in Examples.

FIGS. 7(*a*), 7(*b*) and 7(*c*) show electropherograms of which an amplifiable amount of a trace amount of mRNA was studied.

As shown in FIGS. 7(*a*) and 7(*b*), even in a case where the amount of the trace amount of mRNA (purified from a 293T cell) is approximately 0.1 ng, or even if the amount of the trace amount of mRNA is approximately 0.01 ng, it was demonstrated that the cDNA were efficiently synthesized.

Moreover, as shown in FIG. 7(*c*), the cDNA is efficiently synthesized even in a case of a Hela cell-purified trace amount of mRNA.

Result 3

Figure 8:
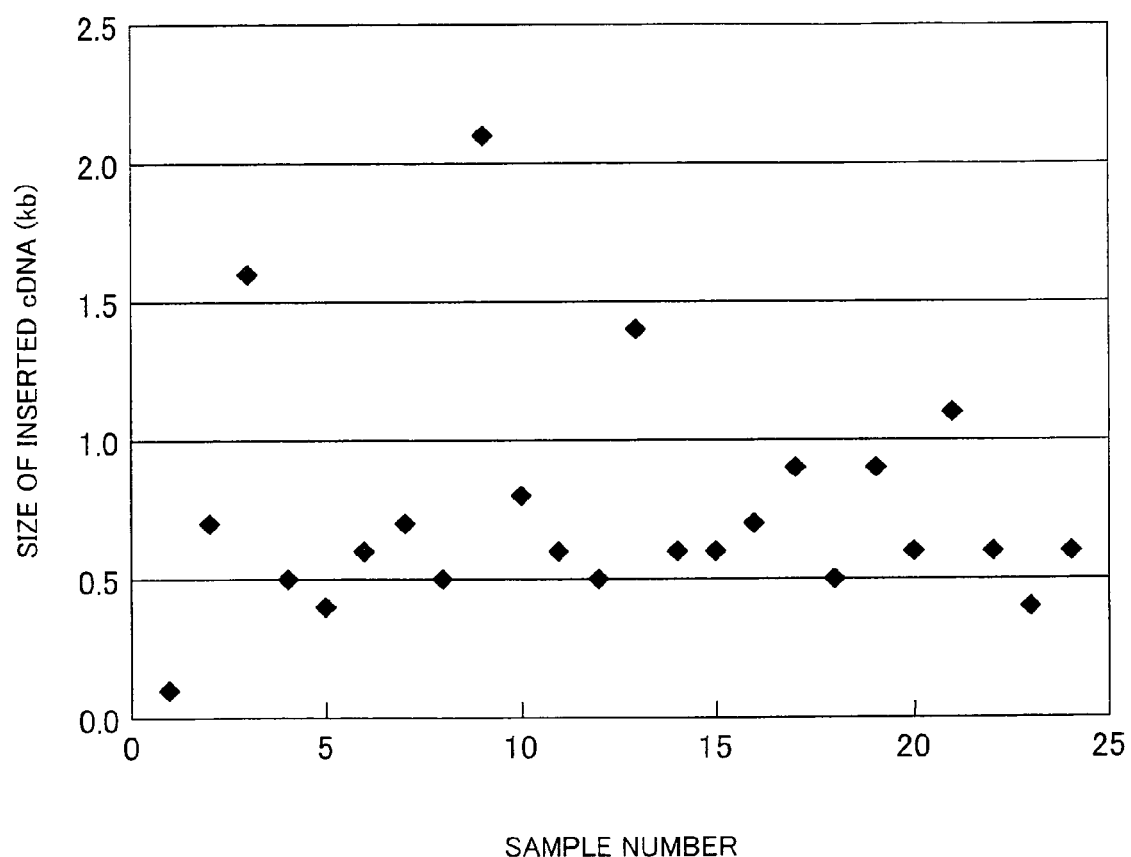
FIG. 8 is a graph showing a length distribution of inserts of a cDNA library in Examples.

FIG. 8 shows a distribution of a length of an insert of the cDNA library. In Example, colonies of $6.6 \times 10^5$ cfu were attained. Insert insertion rate was studied for these colonies, which resulted as 38.3% (23 clones out of 60 clones). Moreover, 15 clones of the 23 clones had a human gene inserted therein, and among the 15 clones, just 2 clones inserted an identical gene (Sample 3 of Table 1).

As shown in FIG. 8, it was demonstrated that the cDNA library prepared in the method in the invention had a long insert. An average length of the insert was 0.75 kb.

A result which reads a sequence of the inserts in the cDNA library is as shown in Table 1.

TABLE 1

| Accession # | Gene Name |
|---|---|
| NM_021103 | thymosin, beta 10 (TMSB10) |
| NM_021104 | ribosomal protein L41 (RPL41) |
| NM_170784 | McKusick-Kaufman syndrome (MKKS), transcript variant 2 |
| NM_001009 | ribosomal protein S5 (RPS5) |
| BC007845 | lysosomal-associated membrane protein 1, mRNA (cDNA clone IMAGE: 4128923) |
| NM_001042465 | prosaposin (variant Gaucher disease and variant metachromatic lenkodystrophy (PSAP) |
| NM_079423 | myosin, light polypeptide 6, alkali, smooth muscle and non-muscle (MYL6) |
| NM_002291 | laminin, beta 1 (LAMB1) |
| NM_007173 | protease, serine, 23 (PRSS23) |
| NM_032937 | chromosome 9 open reading frame 37 (C9orf37) |
| NM_003757 | eukaryotic translation initiation factor 3, subunit 2 beta, 36 kDa (EIF3S2) |

TABLE 1-continued

| Accession # | Gene Name |
|---|---|
| NM_002018 | flightless I homolog (*Drosophila*) (FLII) |
| NM_003589 | cullin 4A (CUL4A) |
| NM_018462 | chromosome 3 open reading frame 10 (CSorf10) |

Further, a quality of the cDNA library prepared by the method of the invention of the present application was compared with a quality of a cDNA library prepared by a conventional method (Kobori M et al., Genes Cells, 1998; 3: 459-475) which uses mRNA extracted from 1 million 293T cells.

More specifically, a study was made by use of the PCT method for 28 randomly selected genes, of whether or not the gene is included in the library.

Table 2 lists the genes which were included in both the cDNA library prepared in the method of the invention of the present application and the cDNA library prepared in the conventional method.

TABLE 2

| Accession # | Gene Name |
|---|---|
| XM_165877 | oxoglutarate (alpha-ketoglutarate) dehydrogenase (lipoamide) (OGDH) |
| NM_023018 | NAD kinase (NADK) |
| CR598431 | GRB2-related adaptor protein 2 (GRAP2) |
| NM_005238 | v-ets erythroblastosis virus E26 oncogene homolog 1 (avian) (ETS1) |
| NM_004383 | c-src tyrosine kinase (CSK) |
| NM_016263 | fizzy/cell division cycle 20 related 1 (*Drosophila*) (FZR1) |
| AF029082 | 14-3-3 sigma |
| U20972 | 14-3-3 epsiron |
| NM_002350 | v-yes-1 Yamaguchi sarcoma viral related oncogene homolog (LYN) |
| NM_001030 | ribosomal protein S27 (metallopanstimulin 1) (RPS27) |
| NM_001157 | annexin A11 (ANXA11) |
| NM_001016 | ribosomal protein S12 (RPS12) |
| NM_021149 | coactosin-like 1 (*Dictyostelium*) (COTL1) |
| NM_001006 | ribosomal protein S3A (RPS3A) |
| NM_004707 | APG12 autophagy 12-like (*S. cerevisiae*) (APG12L) |
| NM_003794 | sorting nexin 4 (SNX4) |
| NM_001003 | ribosomal protein, large, P1 (RPLP1) |
| BC016148 | integral membrane protein 2B (ITM2B) |
| NM_005534 | interferon gamma receptor 2 (interferon gamma transducer 1) (IFNGR2) |
| NM_004396 | DEAD/H (Asp-Glu-Ala-Asp/His) box polypeptide 5 (RNA helicase, 68 kDa) (DDX5) |
| NM_007104 | ribosomal protein L10a (RPL10A) |
| NM_012433 | splicing factor 3b, subunit 1, 155 kDa (SF3B1) |
| NM_005737 | ADP-ribosylation factor-like 4C (ARL4C) |
| NM_014338 | phosphatidylserine decarboxylase (PISD) |
| NM_016505 | putative S1 RNA binding domain protein (PS1D) |

As shown in Table 2, 25 of the 28 genes were included in both of the libraries.

Table 3 shows genes that were only included in the cDNA library prepared by the conventional method.

TABLE 3

| Accession # | Description |
|---|---|
| AL117596 | cDNA DKFZp564C2163 |
| XM_371848 | chromosome 6 open reading frame 115 (C6orf15) |
| NM_004798 | kinesin family member 3B (KIF3B) |

As clear from Tables 1 through 3, the cDNA library prepared by the method of the invention in the present application demonstrates that various inserts are inserted. Moreover, it is demonstrated that the cDNA library prepared by the method of the invention in the present application includes genes which have low expression amount in a cell.

That is to say, a library prepared by the method of the invention in the present application has variety, insertion efficiency and average strand length which compare favorably with a library prepared by use of a large amount of mRNA.

Result 4

Evaluation was carried out by use of a bioanalyzer (Bioanalyzer 2100) produced by Agilent, which is capable of accurate analysis of the trace RNA, regarding size bias of a cDNA pool amplified by the dummy RNA, and an improvement effect of an mRNA amplification efficiency.

More specifically, a first amplification of the mRNA was carried out by use of the dummy RNA, and thereafter, an amplification of GAPDH was confirmed by the PCR method. Further, a second amplification of the mRNA was carried out by use of the amplified mRNA and the dummy RNA, and thereafter an mRNA amplification effect of the dummy RNA was studied.

After preparation of a double strand DNA for amplification by following the aforementioned protocol, an amplification of a labeled cRNA was carried out by use of a fluorescent dye (Cy5). Thereafter, an experiment result was displayed by use of an electropherogram (superposition).

Figure 9A:
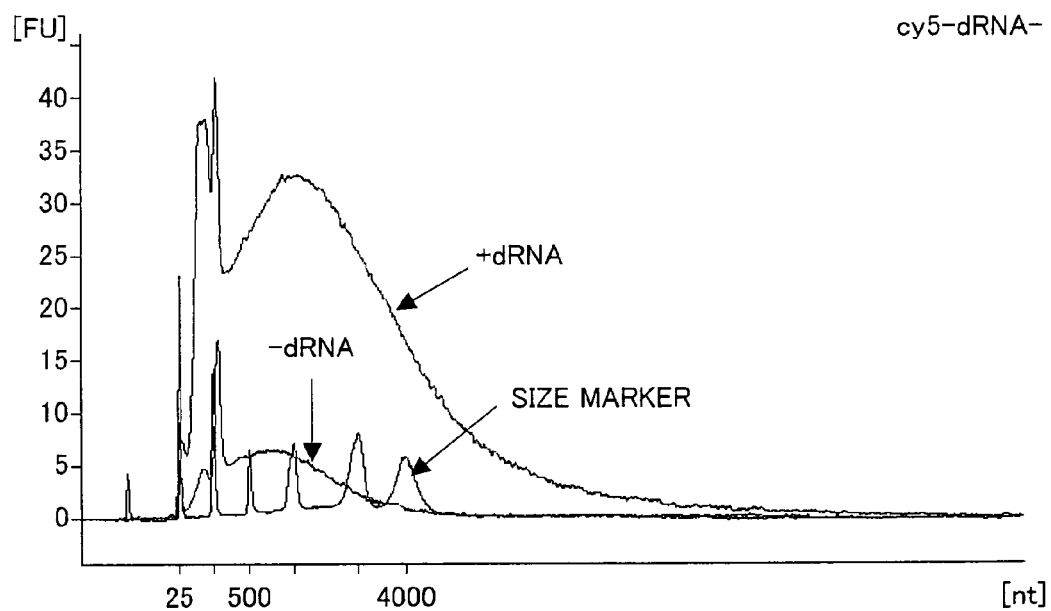
FIG. 9(a) is a graph showing a size distribution of amplified mRNAs.
Figure 9B:
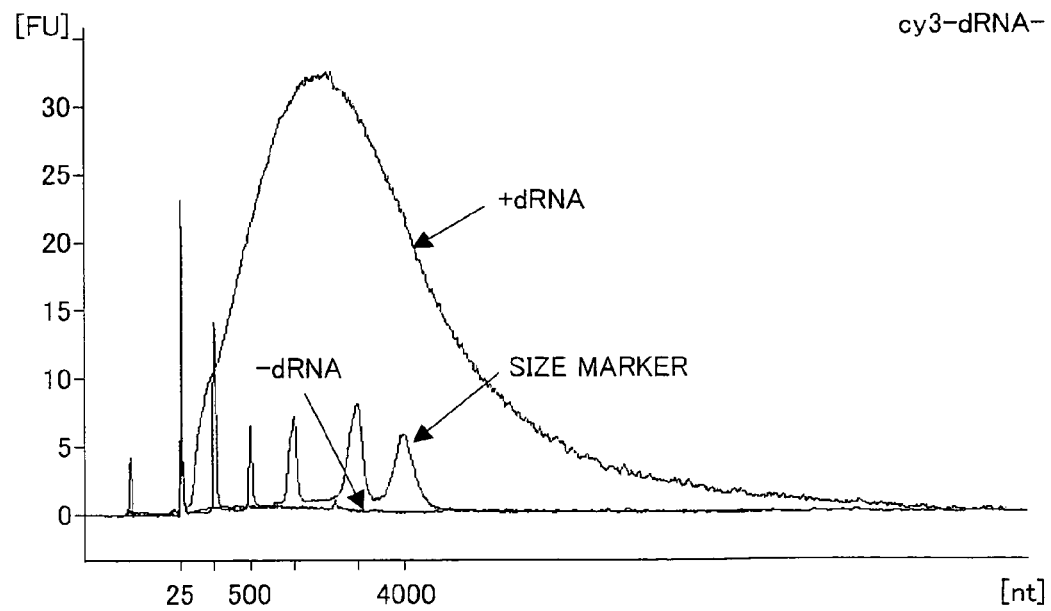
FIG. 9(b) is a graph showing a size distribution of amplified mRNAs.

As a result, as shown in FIG. 9(a), an improvement in amplification of not less than 6 fold as compared to an amplification without the dummy RNA was observed in the cRNA amplified by use of the dummy RNA. Even in a similar experiment using a different fluorescent dye (Cy3) carried out just in case, an amplification effect of not less than 30 fold was recognized in the case where the dummy RNA was used (blue line) (see FIG. 9(b)).

A green line indicates a peak of an RNA ladder, and it is observed that two blue lines in which the dummy RNA were added is transcribed and amplified more efficiently than the case without the dummy RNA, for not less than 4 kb. This result demonstrates that, due to the addition of the dummy RNA, the cDNA conversion by a reverse transcriptase occurred with a small number of mRNA, and the enzyme reaction in the transcript amplification by the T7 RNA polymerase took place evenly to a broad range of the mRNA. This indicates that the technique which uses the dummy RNA is more excellent than the PCR method associated unavoidably with unevenness in amplification.

Result 5

A study was carried out by use of cDNA microarray (dichroic method, Dyeswap method) of Agilent, in order to examine whether types of mRNA in a nano cDNA library prepared by use of the dummy RNA includes a gene which has uneven amplification.

More specifically, a nano cDNA library (+dRNA) amplified from a infinitesimal RNA equivalent to 10 HeLa cells and a cDNA library (−dRNA) prepared by following a conventional method using a large amount of mRNA purified from around 1 million HeLa cells were compared.

First, mRNA was transcribed by the T7 RNA polymerase by use of a plasmid DNA derived from both of the cDNA libraries. Thereafter, the mRNA was processed by use of a DNase that is free of the RNase.

Figure 10A:
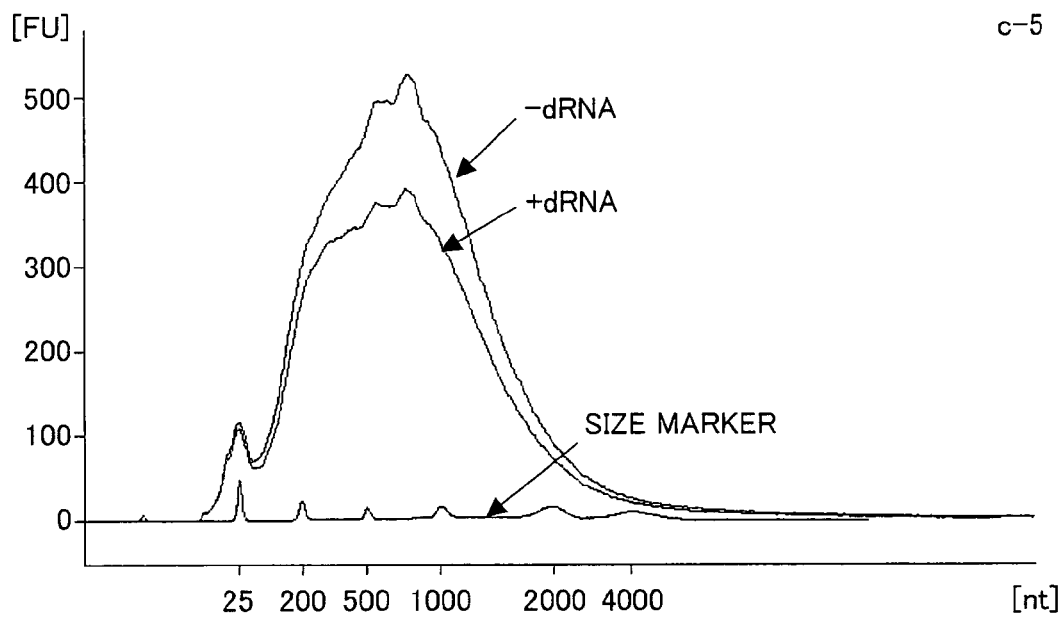
FIG. 10(a) is a graph showing a comparison of size distributions of amplified mRNAs.
Figure 10B:
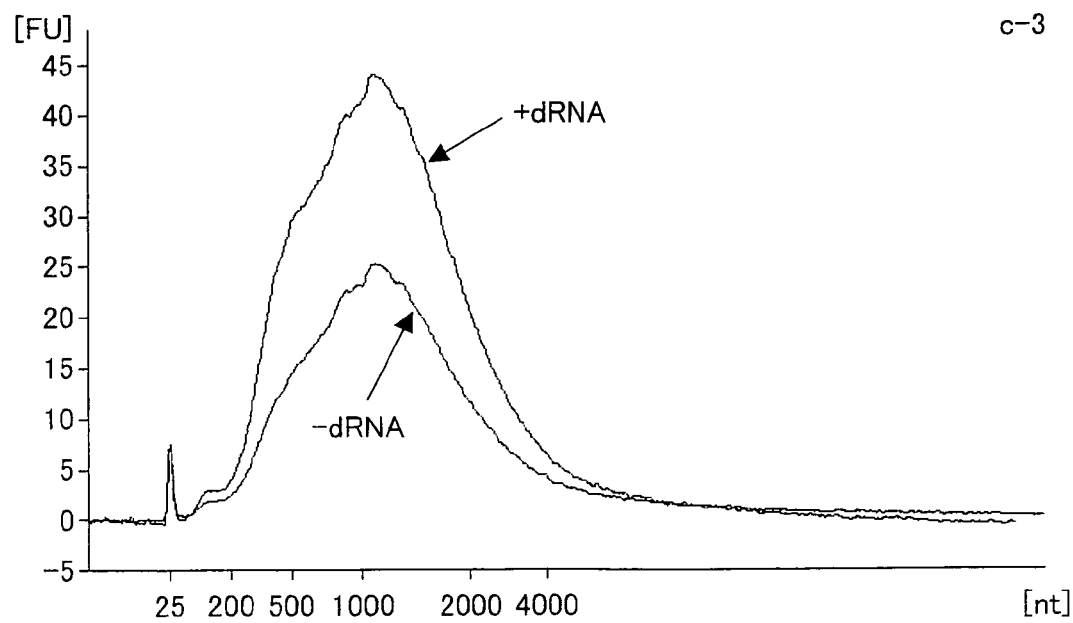
FIG. 10(*b*) is a graph showing a comparison of size distributions of amplified mRNAs.

From the mRNA as a sample, a double strand DNA for amplification was prepared by following the aforementioned protocol. Thereafter, amplification of a labeled cRNA was carried out by use of a fluorescent dye (Cy5). An RNA concentration of the cDNA libraries was measured, which gave measurements of 0.60 mg/ml for the nano cDNA library, and 0.53 mg/ml for the regular nano cDNA library. A size distribution of the cDNA libraries was evaluated by use of the bioanalyzer (Bioanalyzer 2100). The evaluation showed a similar uptaking rate and distribution pattern throughout the size range, irrespective of which fluorescent dye was used, either a Cy5 label (see FIG. 10(a)) or a Cy3 label (see FIG. 10(b)).

Next, a fluorescent dye swapping experiment (DyeSwap) was carried out by use of a cDNA microarray ("agilent Hu44K" produced by Agilent) which incorporates 44,000 cDNAs. Labeled RNAs were served as a probe. A result of the fluorescent dye swapping experiment was calculated by: (−dRNA/Cy3 vs +dRNA/Cy5)/(+dRNA/Cy3 vs −dRNA/Cy3). More specifically, the result was found by competitively hybridizing two types of samples on one piece of array, which samples were labeled with Cy3 and Cy5, respectively.

Figure 13:
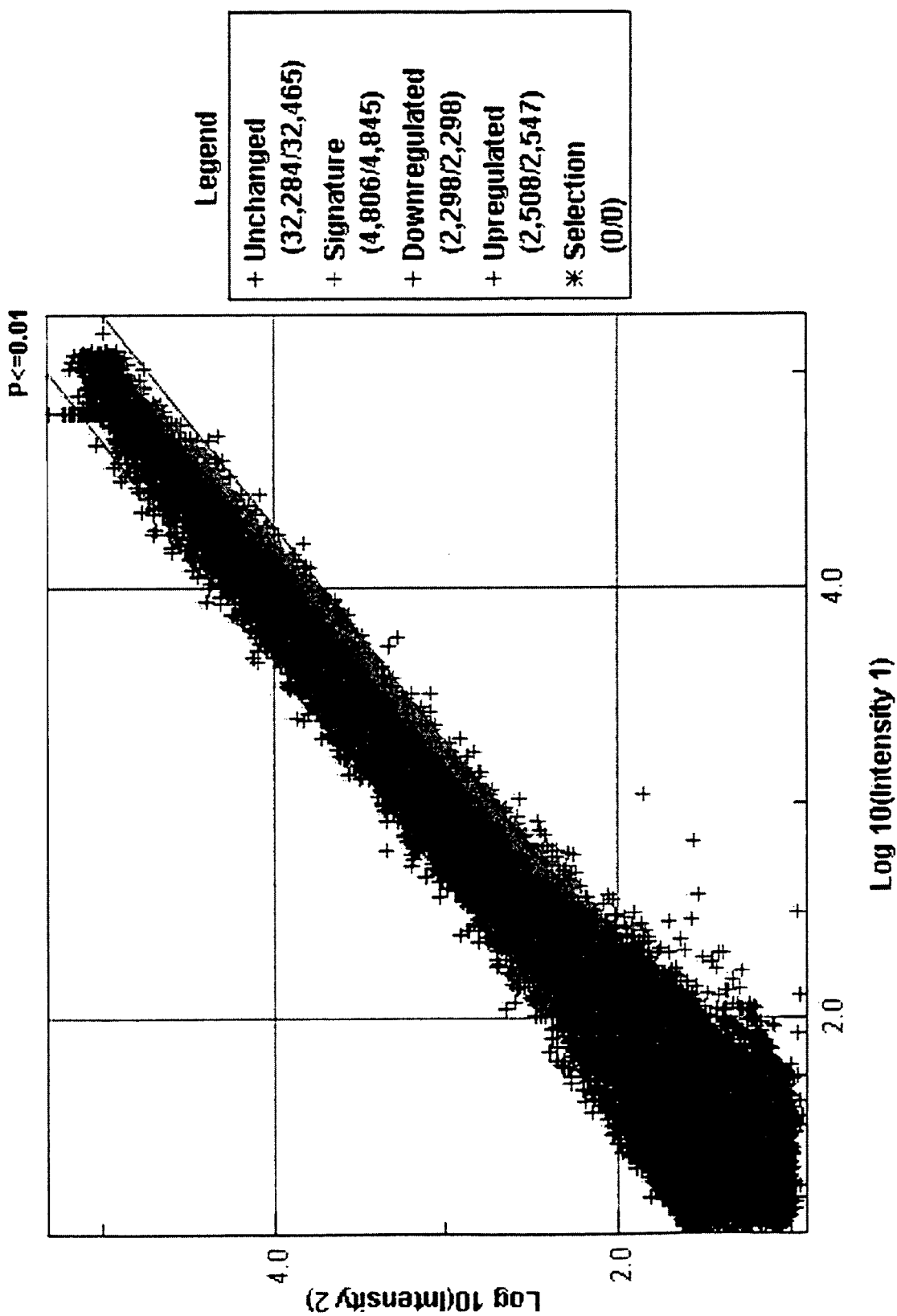
FIG. 13 is a graph showing a result of a fluorochrome exchange experiment in Examples.

FIG. 13 shows a result of the fluorescent dye swapping experiment. In FIG. 13, a gene cluster which has identical fluorescence intensity is shown on a center area in black color; a gene cluster at which a hybridize intensity strengthens in a case where the dummy RNA (dRNA) is added is shown on an upper side in dark gray color; and a gene cluster at which a hybridize intensity weakens by addition of the dummy RNA is shown on a lower side in light gray color.

As a result of comparison between intensity distributions of cDNA in which each of the probes were hybridized, patterns substantially matched except that a few genes differed between the two. This suggests that the cDNA libraries have a substantially same cDNA molecular species are identical qualitatively. Namely, it was ascertained that a nano cDNA library prepared by use of the dummy RNA and having the infinitesimal RNA equivalent to 10 HeLa cells as a starting point is high in quality.

Result 6

The above example studied a case where an mRNA purified from a cell, that is, an mRNA mixture which contains various types of mRNA was amplified. Accordingly, a study was carried out whether or not the method of the invention of the present application is capable of efficiently amplifying one type of mRNA.

As the one type of mRNA, an mRNA of human GAPDH was used. The mRNA of human GAPDH were cloned from a HeLa cDNA library by use of the PCR method, using the following GAPDH S primer and GAPDH AS primer:

```
GAPDH S:
                                      (SEQ ID No. 14)
5'-ACAGTCAGCCGCATCTTCTT-3'

GAPDH AS:
                                      (SEQ ID No. 15)
5'-TTTTTTTTTTTTTTTTTTTTTTTTTTTTTTTTTTGGTTGAGCACA

GGGTACTTTATTG-3'
```

A DNA fragment (approximately 1300 bp) corresponding to the human GAPDH was extracted, and this DNA fragment was cloned into a pT7-Blue vector (Invitrogen Corp., Carlsbad, Calif., USA) using a TA-cloning method.

The vector thus obtained was linearized by digestion with BamHI, and was purified. After purification, RNA was transcribed (at 37° C. for 4 hours) by use of MEG Ascript (produced by Ambion). Thereafter, the vector was digested by DNase treatment using TURBO DNA-free (produced by Ambion) at 37° C. for 1 hour. Subsequently, the RNA thus transcribed was purified.

A double strand DNA for amplification was prepared by using the mRNA of the human GAPDH, by following the steps of [3: Preparation of Double Strand DNA] through [6: Preparation of double strand DNA for amplification]. An amount of the mRNA of the human GAPDH used in the present Example was 4.9 fg, 0.49 fg, 0.049 fg, or 0.0049 fg.

Moreover, the dummy RNA in the present Example was the dummy RNA indicated by the SEQ ID No. 6.

Figure 11:
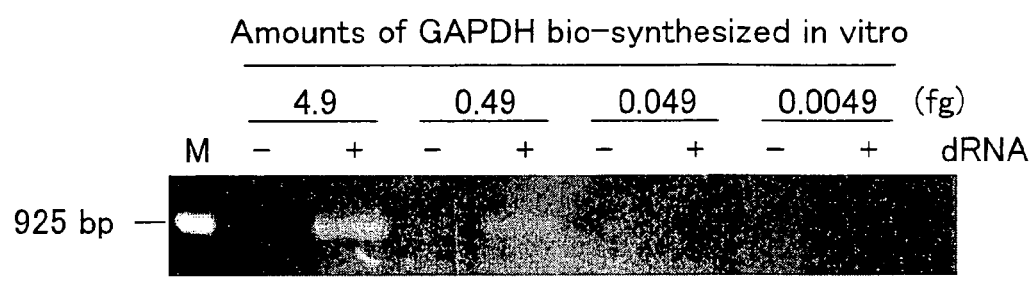
FIG. 11 is an electropherogram showing an amplification effect of one type of RNA, in Examples.

As shown in FIG. 11, the method of the present Example was capable of amplifying an mRNA of a small amount such as 0.49 fg/ml. Note that in FIG. 11, amplification of the mRNA of the human GAPDH by use of the PCR method was also confirmed, which PCR method was carried out with 40 cycles.

Result 7

It was studied whether or not a dummy RNA having a different sequence also attained a similar mRNA amplification effect.

As in the aforementioned steps of [3: Preparation of Double Strand DNA] through [6: Preparation of Double Strand DNA For Amplification], an mRNA (approximately 0.1 ng) purified from ten 293T cells was amplified by use of 1 μg of the dummy RNA indicated by SEQ ID No. 16. The following is a base sequence of the dummy RNA. Note that in FIG. 12, the dummy RNA is shown as "NotI-dRNA".

```
Dummy RNA:
                                        (SEQ ID No. 16)
5'-AATCTGTCGCGGCCGCAAAAAAAAAAAAAAAAAAAAAAAA-3'
```

Figure 12:
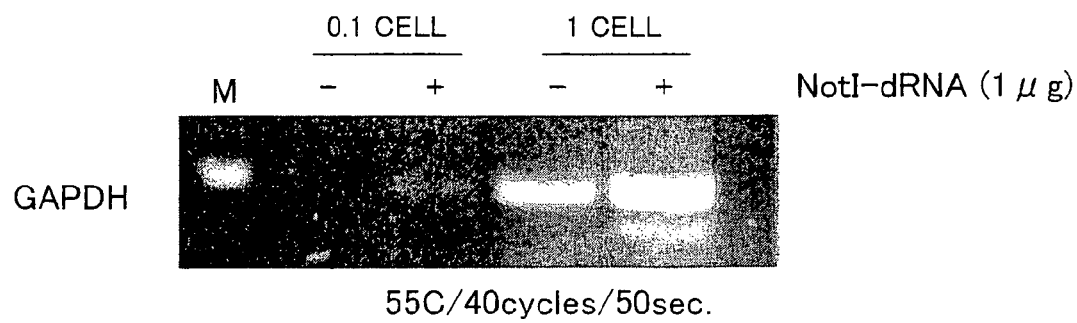
FIG. 12 is an electropherogram showing amplification effects of an mRNA in a case where dummy RNA having different sequences are used, in Examples.

As shown in FIG. 12, it was possible to amplify the mRNA even in a case where the dummy RNA having a different sequence was used, as long as the method of the present Example was used. In FIG. 12, amplification of the human GAPDH mRNA by the PCR method was confirmed, which PCR method was carried out with 40 cycles.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The method of the present invention for amplifying a trace amount of mRNA includes the steps of: (i) adding a dummy RNA to a solution containing the trace amount of mRNA so as to prepare a mixed solution; (ii) synthesizing an anti-sense DNA by reverse transcription, which uses the mixed solution as a template; (iii) synthesizing a sense DNA which is complementary to the anti-sense DNA thus synthesized, so as to generate a double strand DNA made of the sense DNA and the anti-sense DNA; (iv) ligating an RNA polymerase promoter sequence to the double strand DNA thus generated, on a sense DNA 5' end side of the double strand DNA, so as to prepare a double strand DNA for amplification; and (v) amplifying, by using RNA polymerase, an RNA from the double strand DNA for amplification.

According to the method, PCR is not used for amplifying the double strand DNA. Therefore, it is possible to amplify a short and long mRNA at a same efficiency level regardless of how long a base sequence of the trace amount of the mRNA that is to be amplified is. Hence, the method is usable for cDNA library preparation, probe preparation, stepwise subtraction, and the like.

As such, the present invention amplifies the trace amount of the mRNA with the dummy RNA. As a result, the trace RNA is efficiently and evenly amplified. Therefore, the present invention can also be widely applied to fields which require an amplification step of the trace amount of mRNA, meanwhile the present invention is typically useful for: preparation of RT-PCR, cDNA microarray, and cDNA library; amplification of the mRNA (for example, SPIA and the like); preparation of a labeled probe using the mRNA; and stepwise subtraction.

Recent researches turns to nano level analysis which works on one to several cells. Efficient synthesis of cDNA from an extremely small amount of mRNA makes it possible to obtain data detailed to such degree. Therefore, the present invention is usable for (i) studies of stem cells whose availability limited to such a small amount of cells has hinders its gene level analysis, and (ii) analysis of a cause of a disease by using an pathological tissue of a patient. Further, comprehensive isolation of genes which are expressed in one cell becomes possible, by combining the present invention and a multidifferentiation method.

The invention claimed is:

1. A method for amplifying a trace amount of mRNA, comprising:
   adding a dummy RNA to a solution containing the trace amount of mRNA, so as to prepare a mixed solution;
   synthesizing an anti-sense DNA by reverse transcription that uses the RNA in the mixed solution as a template;
   synthesizing a sense DNA which is complementary to the anti-sense DNA thus synthesized, so as to generate a double-strand DNA made of the sense DNA and the anti-sense DNA;
   ligating an RNA polymerase promoter sequence to the double-strand DNA thus generated, on a sense DNA 5' end side of the double-strand DNA, so as to prepare a double-strand DNA for amplification, wherein ligating the RNA polymerase promoter sequence includes ligating the promoter sequence to both ends of the double-strand DNA thus generated, and cleaving the promoter sequence off from the double-strand DNA only on the sense DNA 3' end side; and
   amplifying, by using RNA polymerase, an RNA from the double-strand DNA for amplification.

2. The method for amplifying a trace amount of mRNA as set forth in claim 1, wherein ligating the RNA polymerase promoter sequence includes generating a restriction enzyme site on the double-strand DNA, on the sense DNA 3' end side of the double-strand DNA, so as to cleave the promoter sequence off from the double-strand DNA only on the sense DNA 3' end side.

3. The method for amplifying a trace amount of mRNA as set forth in claim 1, wherein ligating the RNA polymerase promoter sequence includes removing the promoter sequence thus cleaved off and the dummy RNA.

4. The method for amplifying a trace amount of mRNA as set forth in claim 1, wherein the dummy RNA includes a poly(A) sequence.

5. A method for amplifying a trace amount of mRNA, comprising:
   adding a dummy RNA to a solution containing the trace amount of mRNA, so as to prepare a mixed solution; wherein the sequence of the dummy RNA is a base sequence indicated by SEQ ID No. 4, 6, or 16;
   synthesizing an anti-sense DNA by reverse transcription that uses the RNA in the mixed solution as a template;
   synthesizing a sense DNA which is complementary to the anti-sense DNA thus synthesized, so as to generate a double-strand DNA made of the sense DNA and the anti-sense DNA;
   ligating an RNA polymerase promoter sequence to the double-strand DNA thus generated, on a sense DNA 5' end side of the double-strand DNA, so as to prepare a double-strand DNA for amplification; and
   amplifying, by using RNA polymerase, an RNA from the double-strand DNA for amplification.

6. The method for amplifying a trace amount of mRNA as set forth in claim 5, wherein the dummy RNA is biotinylated.

7. The method for amplifying a trace amount of mRNA as set forth in claim 5, wherein the RNA polymerase is T7 polymerase, T3 polymerase, or SP6 polymerase.

8. The method for amplifying a trace amount of mRNA as set forth in claim 5, wherein the dummy RNA is present in the mixed solution at a concentration between 0.5 and 10 μg/μL.

* * * * *

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 1
taatacgact cactataggg aga                                              23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 2
```

```
aattaaccct cactaaaggg                                               20
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 3

```
atttaggtga cactatagaa tac                                           23
```

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 4

```
aattcgtctg gacacgaaaa aaaaaaaaaa aaaaaaaaa agc                      43
```

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 5

```
ggccgctttt tttttttttt tttttttttt tcgtatccag acg                     43
```

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 6

```
aattcgtctg gacacgaaaa aaaaaaaaaa aaaaaaaaa a                        41
```

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 7

```
gagagagaga gagagataat acgactcact atagggaggc ggccgctttt tttttttttt   60
tttttt                                                              66
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 8

```
cgagatccct ccaaaatcaa                                                20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 9

```
aggggtctac atggcaactg                                                20
```

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 10

```
cactagtacg cgtaatacga ctcactatag ggaattcccc ggg                      43
```

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 11

```
cccggggaat tccctatagt gagtcgtatt acgcgtacta gtgagct                  47
```

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 12

```
gatccccggg                                                           10
```

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 13

```
cccggg                                                                6
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 14

```
acagtcagcc gcatcttctt                                                20
```

```
<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 15
tttttttttt tttttttttt tttttttttt tttttggtt gagcacaggg tactttattg        60

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 16
aatctgtcgc ggccgcaaaa aaaaaaaaaa aaaaaaaaaa a                            41
```